United States Patent
Marchuk et al.

(10) Patent No.: US 10,444,156 B2
(45) Date of Patent: Oct. 15, 2019

(54) METHOD FOR DETERMINING THE SURFACE CHARACTERISTICS OF TARGETS

(71) Applicant: FORSCHUNGSZENTRUM JUELICH GMBH, Juelich (DE)

(72) Inventors: Oleksandr Marchuk, Dueren (DE); Christian Brandt, Stralsund (DE); Albrecht Pospieszczyk, Bonn (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/072,505

(22) PCT Filed: Jan. 25, 2017

(86) PCT No.: PCT/DE2017/000003
§ 371 (c)(1),
(2) Date: Jul. 25, 2018

(87) PCT Pub. No.: WO2017/144034
PCT Pub. Date: Aug. 31, 2017

(65) Prior Publication Data
US 2019/0064075 A1 Feb. 28, 2019

(30) Foreign Application Priority Data
Feb. 26, 2016 (DE) .................. 10 2016 002 270

(51) Int. Cl.
*G01N 21/73* (2006.01)
*G01J 3/443* (2006.01)
(Continued)

(52) U.S. Cl.
CPC .............. *G01N 21/73* (2013.01); *G01J 3/443* (2013.01); *G01N 21/66* (2013.01); *G01N 21/71* (2013.01); *H01J 37/32917* (2013.01)

(58) Field of Classification Search
CPC .............. G01N 33/483; G01N 33/487; G01N 33/6896; G01N 21/73; G01N 21/636;
(Continued)

(56) References Cited

U.S. PATENT DOCUMENTS 9,983,060 B1 * 5/2018 Zhao .................... G01N 21/274
2017/0105276 A1 * 4/2017 Kock ..................... H05H 3/00

OTHER PUBLICATIONS

John R. Howell, et al., Thermal Radiation Heat Transfer, Fifth Edition, Dec. 2011, pp. 69-70.
(Continued)

*Primary Examiner* — Michael P Stafira
(74) *Attorney, Agent, or Firm* — Leydig, Voit & Mayer, Ltd.

(57) ABSTRACT

A method for in situ determination of surface characteristics of conductive targets includes generating a low-pressure plasma in front of a surface of a target, applying a voltage to the surface of the target, orientating at least one light-sensitive detector at an angle θ relative to a perpendicular to the surface of the target, and measuring an intensity of light emitted by electrically neutral atoms generated by conversion from ions which are accelerated out of the low-pressure plasma by the applied voltage toward the surface of the target and subsequently reflected thereon, and which thus exchange suitable charges with the surface to reach electrical neutrality. The method additionally includes determining a value curve comprising wavelengths and an intensity associated with each wavelength, of the light which, as a result of Doppler shifts, has a red-shifted wavelength range and a blue-shifted range.

16 Claims, 12 Drawing Sheets

(51) Int. Cl.
- *G01N 21/71* (2006.01)
- *H01J 37/32* (2006.01)
- *G01N 21/66* (2006.01)

(58) Field of Classification Search
CPC .......... G01N 21/66; G01N 21/71; G01N 2201/0675; G01N 2333/916; G01N 2500/04; G01N 33/57484; G01N 2021/655; G01N 21/17; G01N 21/35; G01N 21/55; G01N 21/6428; G01N 2291/0258; G01N 2291/044; G01N 29/14; G01N 29/4436; G01N 33/49; G01N 2021/3111; G01N 2021/8477; G01N 21/3504; G01N 21/87; G01N 23/20; G01N 33/48721; G01J 2003/125; G01J 3/443; G01J 3/32889; H01J 37/32917; H01J 37/32926; H01J 37/32954; H01J 37/32972; H01J 37/147; H01J 49/105; H01J 37/32357; H01J 2237/334; H01J 2237/332; H01J 37/32449; H01J 37/32495; H01J 37/32963; H01J 2237/327; H01J 37/3244; H01J 37/32715; H01J 37/32816; H01J 37/32908; H01J 2237/0203; H01J 2237/057; H01J 2237/0817; H01J 2237/3321; H01J 37/05; H01J 37/08; H01J 37/32027; H01J 37/32082; H01J 37/321; H01J 37/32192; H01J 37/32201; H01J 37/32467; H01J 37/32477; H01J 37/32697; H01J 37/32825; H01J 37/32935; H01J 37/3299; H01J 37/3402; H01J 37/3405; H01J 2237/0802; H01J 2237/14; H01J 2237/152; H01J 2237/3323; H01J 2237/3327; H01J 2237/335; H01J 2237/338; H01J 27/18; H01J 37/023; H01J 37/14; H01J 37/3053; H01J 37/3171; H01J 37/32009; H01J 37/32018; H01J 37/32045; H01J 37/32055; H01J 37/32064; H01J 37/32146; H01J 37/32229; H01J 37/32321; H01J 37/32422; H01J 37/32522; H01J 37/32532; H01J 37/3255; H01J 37/32568; H01J 37/32614; H01J 37/32633; H01J 37/3266; H01J 37/32669; H01J 37/32724; H01J 37/32862; H01J 37/32871; H01J 37/32944; H01J 37/3408; H01J 37/3441; H01J 37/3447; H01J 37/3452; H01J 37/3458; H01J 49/0031; H01J 49/10; H01J 49/12; H01J 49/40

See application file for complete search history.

(56) References Cited

OTHER PUBLICATIONS

F. Arefi-Khonsari, et al., "Processing polymers by plasma technologies", Surface & Coatings Technology 200, Dec. 2005, pp. 14-20.

S.F. Miralai, et al., „LaMnO$_3$ perovskite thin film deposition, from aqueous nitrate solutions of La and Mn, in a low-pressure plasma expanded through a nozzle (PETN), Thin Solid Films 303, Dec. 1997, pp. 17-26.

Nikolay Britun, et al., "Plasma diagnostics for understanding the plasma-surface interaction in HiPIMS discharges: a review", J. Phys D: Appl. Phys 47, Dec. 2014, 224001 (46pp), pp. 1-46.

C Brandt et al: "Fast non-Maxwellian atoms in a linear magnetized plasma", $42^{nd}$ EPS Conference on Plasma Physics, 2015, Dec. 2015, pp. 1-4, XP055361557.

Minja R. Gemiisc Adamov, et al., "Doppler Spectroscopy of Hydrogen and Deuterium Balmer Alphas Line in an Abnormal Glow Discharge", IEEE Transactions on Plasma Science, vol. 31, No. 3, Jun. 2003, pp. 444-454, XP055362214.

Hans Henrik Andersen, et al., „Angular Distribution of Particles Sputtered from Cu, Pt and Ge Tragets by keV Ar$^+$ Ion Bombardment*, Nuclear Instruments and Methods in Physics Research B6, Dec. 1985, pp. 459-465.

René Feder, et al., "Ion beam sputtering of Ag—Angular and energetic distributions of sputtered and scattered particles", Nuclear Instruments and Methods in Physics Research B 316, Dec. 2013, pp. 198-204.

Catherine C. Cooksey, et al., "Bidirectional reflectance scale comparison between NIST and PTB", applied optics, vol. 54, No. 13, May 1, 2015, pp. 4006-4015.

James F. Ziegler, et al., SRIM—The stopping and range of ions in matter (2010), Nuclear Instruments and Methods in Physics Research B 268, Dec. 2010, pp. 1818-1823.

Alfold TL, et al., "Atomic Collisions and Backscattering Spectrometry", Fundamentals of Nanoscale Film Analysis, Dec. 2007, pp. 12-33.

T. Babkina, et al., "Energy analysis of hyperthermal hydrogen atoms generated through surface neutralization of ions",Europhysics Letters, 72(2), Oct. 15, 2005, pp. 235-241.

M. Gemisic Adamov, et al., "Intensity dependence of hydrogen Lyman alpha and Balmer alpha lines upon cathode material of an abnormal glow discharge", Eur. Phys. J. D 28, December, 2204, pp. 393-398.

A. V. Phelps, "Energetic ion, atom, and molecule reactions and excitation in low-current H$_2$ discharges: Model", Physical Review E 79, Dec. 2009, pp. 066401-1-066401-19.

A. Kreter, et al., "Linear plasma device PSI-2 for plasma-material interaction studies", Fusion Science and Technology, vol. 68, Jul. 2015, pp. 8-14.

* cited by examiner

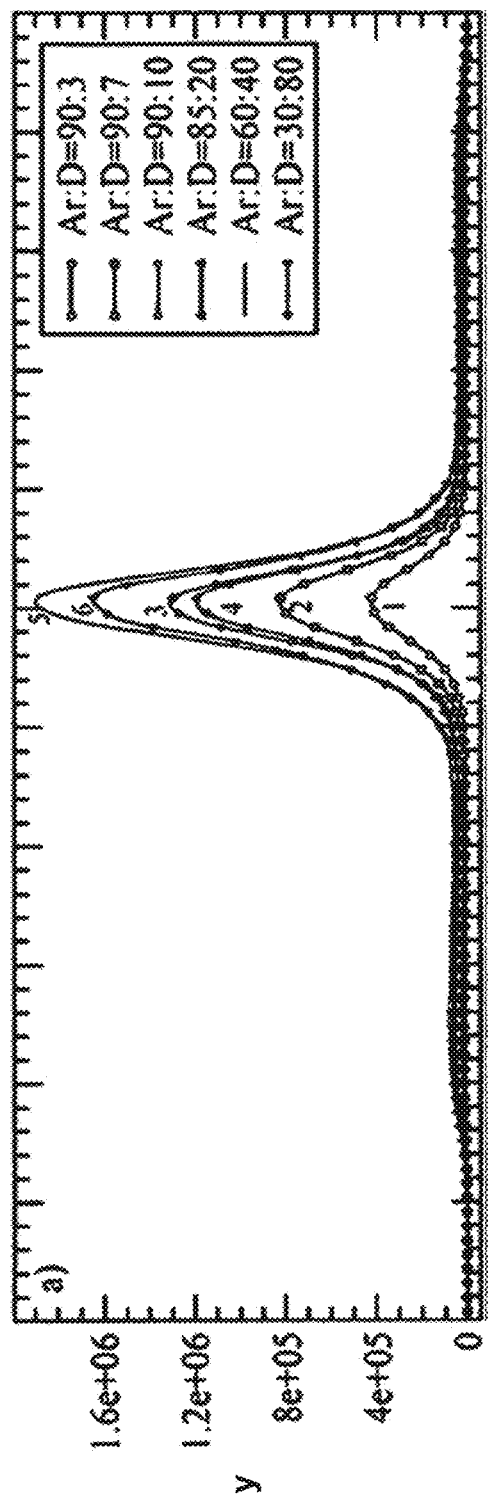
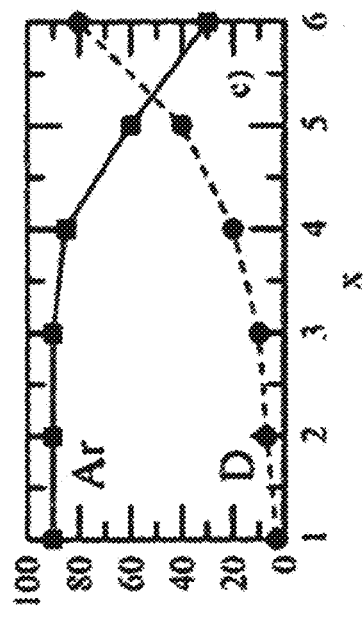
Fig. 5a
Fig. 5c

METHOD FOR DETERMINING THE SURFACE CHARACTERISTICS OF TARGETS

CROSS REFERENCE TO RELATED APPLICATIONS

This application is a U.S. National Stage Application under 35 U.S.C. § 371 of International Application No. PCT/DE2017/000003 filed on Jan. 25, 2017, and claims benefit to German Patent Application No. DE 10 2016 002 270.1 filed on Feb. 26, 2016. The International Application was published in German on Aug. 31, 2017 as WO 2017/144034 A1 under PCT Article 21(2).

FIELD

The invention relates to a method and a device for in situ determination of surface characteristics of conductive targets.

BACKGROUND

Technical plasmas are increasingly being made use of in industry and in research laboratories, and are used among other things for producing high-tech products such as microchips in EUV lithography, for cleaning various surfaces and materials in medical physics, and for coating mirrors in the production of optical elements. Technical plasmas include for example hollow cathode discharges, RF discharges, magnetron discharges, corona discharges and linear discharge arrangements. The reflectivity of metal, generally reflective surfaces plays a very important role in the monitoring and checking of certain production processes.

Hereinafter, the reflectivity of surfaces is divided into two subject areas: the reflection of particles (atoms) and the reflection of light (photons). The reflection of the plasma particles on the surface is an irresistible process which takes place as a result of the interaction between the plasma ions and the surface. Depending on the desired technical production processes, this interaction may have positive and negative effects. For example, in the production of the mirrors, the substrates (Fe, W, Mo) are specially coated (Al, Au or Ag). By contrast, the coating with plasma impurities or the erosion of the substrate are negative, generally unintended effects on the surface. The characteristics of the particle reflection, such as energy distribution and angular distribution of the reflected plasma particles, can provide information regarding the state of the surface, such as the type of material or the roughness [1, 2]. Further diagnostic access comes from the spectral reflectivity of optical metal mirrors and reflective surfaces [3]. This can be made use of to check the efficiency of the technical process. For example, various optical systems are made use of so as to quantify the production processes and control them better using cameras and special instruments (spectrometers). Quite often, the plasma parameters are also determined in the process. These also include very complex optical labyrinths consisting of a plurality of mirrors. The most important limiting case of spectral reflection is specular reflection, in other words mirror reflection, or a purely diffuse reflection and the polarization characteristics thereof [4]. Using appropriate theoretical models, other physical parameters of the surface, such as the roughness, can be determined on the basis of the physical variables, such as the energy and the angular distribution of the particles.

So as to obtain quantified predictions as to the progression of the process, it is necessary to determine the reflectivity of the surface on an ongoing basis during the process [3]. The biggest problem in this context is the fact that the material usually has to be removed from the plasma for this purpose, and the plasma operation thus has to be interrupted.

Simultaneous measurements of the particle reflection and light reflection can only be united in a single laboratory experiment at great complexity, since the characteristics of photons and atoms are so different. Different methods are therefore used for determining the particle reflection and light reflection characteristics. Thus far there is no method which makes it possible to determine or measure both parameters, in other words to approximately measure the reflection of particles and of photons in situ in the plasma without additional means.

To determine the energy distribution and angular distribution of reflected atoms on a surface, ion irradiation of the surface is combined either with laser-induced fluorescence (LIF) or with an energy-mass detector. The measuring setup is shown schematically in FIG. 1.

Initially, the ions striking the surface are neutralized. The neutral atoms leave the surface with an energy less than the ion incidence energy (E0). The atoms are backscattered in a particular energy distribution f(E<E0). Observation of the reflection at different angles provides the angular distribution of the reflected atoms. The theoretical description of the particle reflection process can be calculated using Monte Carlo simulations, such as the TRIM or SRIM code [5]. In general, a close correspondence to the measured data is found in this way. At this point, it should now be noted that the roughness of a surface and any coating thereof strongly influence the results of this distribution. As a result, the angular distribution and energy distribution of the scattered particles during the plasma operation are irreplaceable measurement variables [3].

In the case of reflecting surfaces, it is a question not just of the reflected particles, but also of the spectral or specular reflection of light. So as to be able to answer this question, a large number of spectrophotometric instruments are available here. All in all, the measurement of the reflectivity of various materials is one of the most important tasks in spectrophotometry [3]. The sketch in FIG. 2(a) shows the basic progression of measurements of this type, although the details may vary between different instruments [3].

Before placement in the plasma, the mirror is carefully measured for reflectivity in the mirror laboratory. While an absolutely calibrated light source is illuminating the mirror, the reflection is measured at the angles which are subsequently used in the production process. FIG. 2(b) shows how the mirror is subsequently placed in the plasma chamber and the plasma switched on. The production process is monitored by the detector B. As a result of the contact with the plasma, the reflectivity may change over time. Because of the constantly occurring collisions of the plasma particles (or because of the particles of impurities) with the surface of the mirror, in most cases the reflectivity of said surface becomes worse. However, it is not possible to remeasure the reflectivity in situ, since the technical process usually has to be interrupted for this purpose. Instead, the mirror has to be removed from the plasma and tested in the laboratory again, repeating the loop shown in FIG. 1. For targeted coating processes, or else if an operating error occurs, the material has to be removed from the plasma again so as to determine the reflectivity once again.

There are applications in which it is not possible to open the plasma chamber and repeat the measurement of the reflectivity in accordance with FIG. 1. These include processes in toxic or radioactive environments. New measurements of the reflectivity of the surface of particles and photons in environments of this kind may not be possible in practical terms or else simply involve high costs and expenditure of time. Some major projects planned for the future, such as the fusion experiment ITER or the experimental reactor DEMO, will have to deal with radioactively activated materials. For the surfaces subsequently exposed to the plasma, the consequences are even more serious, since information regarding the states of the surfaces (walls, substrates and mirrors) cannot be exactly predicted.

SUMMARY

In an embodiment, the present invention provides a method for in situ determination of surface characteristics of conductive targets. The method includes a) generating a low-pressure plasma in front of a surface of a target; b) applying a voltage to the surface of the target; c) orientating at least one light-sensitive detector at an angle θ relative to a perpendicular to the surface of the target; d) measuring an intensity of light emitted by electrically neutral atoms generated by conversion from ions which are accelerated out of the low-pressure plasma by the applied voltage toward the surface of the target and subsequently reflected thereon, and which thus exchange suitable charges with the surface to reach electrical neutrality; e) determining a value curve comprising wavelengths and an intensity associated with each wavelength, of the light which, as a result of Doppler shifts, has a red-shifted wavelength range having smaller wavelengths than a wavelength $\lambda_0$ of the light emitted by atoms stationary relative to the detector and a blue-shifted range having wavelengths greater than $\lambda_0$; f) determining a velocity v of a atoms which emit light of a wavelength $\lambda$ from the value curve using $$v = \frac{\lambda}{\lambda - \lambda_0} \cdot c,$$

where c is she speed of light, and from this determining respective kinetic energies E of the atoms using $\varepsilon = 1/2 m_2 v^2$, where $m_1$ is a mass of each of the reflected atoms; g) determining an energy value $E_{max}$ as a smallest of the measured wavelengths of a particular energy from which all values of the intensity of the value curve are greater than or equal to an intensity value of background noise of the detector signal; and h) determining a mass $m_2$ of atoms of the surface using the formula $$E_{max} = \left[ \frac{(m_2^2 - m_1^2 \sin^2\theta)^{1/2} - m_2 \cdot \cos\theta}{m_3 + m_2} \right]^2 \cdot E_0,$$

where E0 is the kinetic energy of each of the ions upon striking the surface and is equal to the absolute value of the applied voltage.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 5a) shows value curves over the entire measured intensity range of reflected deuterium atoms at an angle of 35° to the surface normal of a tungsten (W) substrate for different mixing ratios of argon and deuterium;

FIG. 5c) shows values of the gas flows corresponding to these mixing ratios;

DETAILED DESCRIPTION

Figure 1:
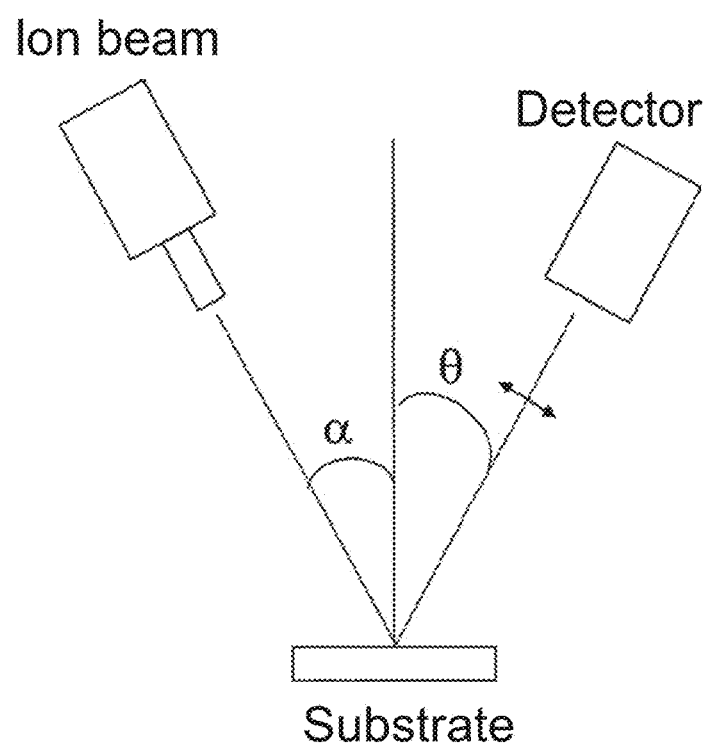
FIG. 1 shows a measurement setup for determining the energy distribution and angular distribution of scattered particles on a substrate surface.

Embodiments of the invention provide methods for in situ determination of the surface characteristics of conductive targets that allow for simultaneous measurement of particle reflection and light reflection. Embodiments of the invention further provide devices for carrying out such methods.

According to an embodiment, the invention provides a method for in situ determination of the surface characteristics of conductive targets, the method including the following steps:
  a) generating a low-pressure plasma in front of the surface of the target
  b) applying a voltage to the surface of the target
  c) orientating at least one light-sensitive detector at an angle θ relative to the perpendicular to the surface of the target
  d) measuring the intensity of the light emitted by the electrically neutral atoms generated by conversion from the ions which are accelerated out of the low-pressure plasma by the applied voltage toward the surface of the target and subsequently reflected thereon, and thus exchange suitable charges with the surface to reach electrical neutrality
  e) determining a value curve comprising the wavelengths and the intensity, associated with each wavelength, of the light which, as a result of Doppler shifts, has a red-shifted wavelength range having smaller wavelengths than the wavelength $\lambda_0$ of the light emitted by atoms stationary relative to the detector and a blue-shifted range having wavelengths greater than $\lambda_0$
  f) determining the velocity v of the atoms which emit light of a wavelength λ from the value curve using $$v = \frac{\lambda}{\lambda - \lambda_0} \cdot c,$$

where c is the speed of light, and from this determining the respective kinetic energies E of the atoms using $\varepsilon = 1/2 m_1 v^2$, where $m_1$ is the mass of each of the reflected atoms
  g) determining the energy value $E_{max}$ as the smallest of the measured wavelengths of a particular energy from which all values of the intensity of the value curve are greater than or equal to the intensity value of the background noise of the detector signal
  h) determining the mass $m_2$ of the atoms of the surface using the formula [6]:

$$E_{max} = \left[ \frac{(m_2^2 - m_1^2 \sin^2\theta)^{1/2} - m_2 \cdot \cos\theta}{m_3 + m_2} \right]^2 \cdot E_0,$$

where $E_0$ is the kinetic energy of each of the ions upon striking the surface and is equal to the absolute value of the applied voltage.

In situ measurement methods according to embodiments of the invention for determining the characteristics of the reflection of hydrogen or deuterium atoms on the surface of electrically conductive materials in low-pressure plasmas make it possible to determine the energy distribution and angular distribution of the atoms reflected on the metal surface. In the case of reflecting surfaces or mirrors, it is additionally possible to measure the spectral reflectivity and polarization characteristics of the surface directly. Because of the diagnostic accesses to these measurement variables, such methods can be used in numerous technical processes and laboratory experiments.

Embodiments of the invention provide methods for in situ determination of the reflection characteristics of metal surfaces toward particles and light. Proposed methods make it possible to measure the energy distribution and angular distribution of the hydrogen or deuterium atoms scattered on a metal surface. The spectral (or specular) reflectivity of the surface can be measured directly from the Doppler shift of the blue-shifted and red-shifted components of the induced Balmer lines. Methods according to embodiments of the invention can, for example, advantageously be used for producing mirrors, for generating coatings, and for analyzing the characteristics of surfaces. Equally, it can make possible uninterrupted access to the aforementioned measurement variables for the analysis of surfaces in dangerous, for example toxic or radioactive, environments. For example, one of the possible fields for future applications is the radioactive plasma environment, where the optical components are particularly difficult to access.

Advantageously, using such methods, the surface characteristics, in particular the mass m2 of the atoms of the surface, can be determined in situ while simultaneously measuring the reflected particles and the reflected light. In particular, the distribution of the energy of the reflected particles and the intensity of the reflected light can be determined in situ simultaneously with the mass of the surface atoms. In this context, the variables m1 and m2 are each in particular the average mass of a corresponding atom or the average mass determined by the method.

If the ions in the low-pressure plasma are positive they accept a sufficient number of electrons during the reflection process on the surface, and if they are negatively charged they correspondingly release a sufficient number of electrons, and are thus converted into electrically neutral atoms. The surface of the target may be connected to a power source, and in this way a desired electrical potential can be maintained even during charge exchange with the ions from the low-pressure plasma.

In the context of the application, determining the surface characteristics in situ should be understood to mean that the target is located in the vacuum during the determination and does not leave it.

To calculate the frequency f and energy E of the photons of electromagnetic radiation, the known formula E=hf using Planck's constant h=4.135667662·10−15 eV·s may be used. The relationship between the frequency of a photon f and the wave number or wavelength λ thereof is described in a known manner by the dispersion relation applicable in accordance with the constraints. Alternatively, the wavelength corresponding to each frequency may also be measured using a method known from optics, for example using the diffraction pattern of an optical grating. The relationship for free space can be taken as an approximation, namely λ=c/f, where c is the speed of propagation of light.

The number of photons may be measured using photon detectors, for example making use of the photoelectric effect. Photocathodes are one example of photon detectors. In the context of the application, the term intensity should be understood to mean in particular the number of photons which are measured for example at a particular energy or wavelength. Using mirrors and gratings which have a concave surface, rays of light can be deflected into different surface regions or channels of detectors of this type by diffraction effects, in such a way that a particular wavelength range can be assigned to each channel.

In the context of the application, the term surface characteristics should be understood to mean in particular the shape and the reflection characteristics of a surface toward ions, atoms or light. This may relate to the spectral reflectivity, for example in the case of light, or to the velocity distribution in the case of particles, or generally to the energy distribution after the reflection of particles or light on the surface. In the context of reflections, the surface characteristics also include material characteristics of the surface. In the context of the application, these include in particular the mass of the atoms at the surface of a target.

The noise components of a signal may be removed using methods known from signal processing, such as smoothing methods, for example using LTI filters or else non-linear filters such as rank order filters or sigma filters.

In the context of the application, background noise should be understood to mean the signal of the light intensity as recorded by the detector for energies above the absolute value of the applied voltage or below minus the absolute value of the voltage.

In the context of the application, the purity level should be understood to mean the proportion of atoms, in particular of stable isotopes, of an element in any mixture of different atoms. As described herein, the concept of the purity level can relate in particular to homogeneous targets.

As described herein, a low-pressure plasma can be understood to mean in particular a plasma having a pressure of at most 0.1 pascals. As is known, 1 pascal is equal to 10-5 bar. For generating the low-pressure plasma, all methods known from the prior art may be used.

Alternatively, the energy value Emax may be determined as the lowest measured energy from which all values of the intensity of the value curve are greater than or equal to an intensity value calculated as the sum of the average of the background noise of the detector signal and one, two or three times or another multiple of the standard deviation of the signal of the background noise. When the average and the standard deviation are determined, by the definition according to the invention of background noise, only values above the absolute value of the voltage or below minus the absolute value of the voltage are taken into account. As is known, the standard deviation decreases with longer measurement times or integration times.

Alternatively, the confidence interval may initially be determined within which there is a probability of W of the average of the intensity of the background noise being located. The value of Emax can then be determined as the lowest energy value or lowest measured energy value for which all values of the measured intensity are greater than or equal to the value of the upper bound of the confidence interval. In this context, W is based on the required precision of the determination of Emax. The bounds of the confidence interval can be reduced by way of longer measurement times or a higher number of measurement values. The precision of the determination or measurement can be increased by using longer measurement times.

The target comprises a conductive surface, and so a voltage can be applied to said surface. It is known from the prior art that the plasma potential can be ignored with respect to the applied voltage in a range of −40 V to −500 V or for voltages having a higher absolute value. In this context, the voltage can be converted into the associated energy by multiplying by the elementary charge, as is known from the prior art. In this case, it is possible in particular to obtain the energy in units of electron volts. In particular hydrogen and deuterium ions having a charge number z=1 are considered. For ions having a charge number z having an absolute value greater than 1, as is known, the absolute value of this charge number z has to be multiplied by the voltage and the elementary charge to obtain the associated (kinetic) energy.

To determine the energy value Emax, the binary impacts of the ions from the plasma on the surface are of primary importance, and not multiple reflections. For higher roughness, the measurement times are increased, in such a way that a sufficient number of binary impacts occur. However, this does not pose an obstacle in principle.

Measurement of the surface characteristics is explained in greater detail hereinafter. The reflectivity of surfaces at particular wavelengths in the visible range has successfully been measured using embodiments of the invention in situ in very general conditions in low-pressure plasmas. Two atomic physics effects and one plasma physics effect make it possible to determine both the reflection of hydrogen particles (energy distribution and angular distribution) and the spectral reflection of the Balmer lines thereof.

It is known that plasma ions can be accelerated in an electrical field because of the positive charge thereof.

This principle is applied so as to produce fast ions in front of a surface. For this purpose, a negative electrical potential (up to −500 V) relative to the plasma potential is applied to the surface so as to accelerate the positively charged particles such as H+ or D+ (in other words hydrogen or deuterium ions having a single positive charge). The energy range of the ions (100 eV to 500 eV) corresponds to that of ion beam experiments. To implement the bias voltage, the surface has to be electrically conductive. Metal surfaces therefore present optimum conditions, and also because the surfaces thereof are not heated to a high degree. If the plasma temperature (in other words the plasma ion temperature Ti and the plasma electron temperature Te) or the energy associated with this temperature is much lower than the energy of the accelerated ions E0 (Ti,e/E0<<1), in practice this can be referred to as ion irradiation of the surface. In the laboratory experiments shown in FIG. 1, the backscattered atoms or ions are immediately analyzed in a mass energy detector, and the information on the energy distribution and angular distribution is derived. To implement the in situ measurement method, the following conditions must be met:

i. The energy distribution and angular distribution of the atoms in the plasma must not change or only change very slowly over time in front of the surface.

ii. The number of atoms of this type or the variable linearly associated with the number of atoms is traced by the other special measurement method without interference.

The first condition is only achieved in the case of low-pressure plasmas (the plasma density N is less than $10^{18}$ $m^{-3}$). In this case, the impacts of the fast atoms with the plasma particles are so infrequent that the original angular distribution and energy distribution of the atoms are maintained for a sufficiently long time. Low-pressure plasmas have a further advantage; the electron temperature becomes higher (from 5 eV to 10 eV), in such a way that very complex molecular processes do not occur. Since the molecules dissociate rapidly, in this case the plasma substantially consists only of $H^+$ ions and electrons, so as to maintain the quasi-neutrality. In this case, the energy distribution and angular distribution are only measured from one type of particle, specifically $H^+$ or $D^+$. The conditions of the ion beam experiments are better met.

Fast atoms of this type have in fact been observed in high-pressure plasmas [7, 8]. However, because of the complex molecular physics relating to the occurrence of the excited states of atoms, as well as a very strong and unknown inhomogeneity of the ion types ($H^+$, $H_2^+$, $H_3^+$) and the thermalization thereof by high plasma density, measurements of the energy distribution and angular distribution of $H^+$ ions are not possible in these plasmas [7, 8, 9]. Therein, it is not possible to quantify the processes in such a way that they can be applied directly to the question underlying the invention.

However, the drawback of low-pressure plasmas is that the flow of plasma ions with respect to the substrate or the surface is so low that the atoms in the plasma cannot be traced using conventional diagnostics. According to embodiments of the invention, the intensity of the Balmer lines of the hydrogen atoms has successfully been greatly increased. In this context, an energy resonance between the metastable states of noble gas atoms and the excited states of hydrogen atoms is made use of [10]:

$$Rg^* + H \rightarrow Rg + H^*. \quad (A)$$

In this context, Rg* is a noble gas flow (Rg=Ar, Kr, He, Ne, Xe) in the excited state, and H* is an H or D atom in the excited state. By way of reaction (A), the emission of the Balmer lines of the reflected atoms can be increased so greatly that these atoms and thus the energy distribution and angular distribution thereof can be effectively determined in low-pressure plasmas. Condition (ii) is thus fully met. Embodiments of the invention provide methods for observing the energy distribution and angular distribution of the reflected H and D atoms. The observation is possible in the mixed plasmas Ar—H, Kr—H or Ar-D, Kr-D. If other noble gases are used, the resonance is very weak and barely measurable, and this is thus associated with much longer measurement times (longer integration times).

Methods according to embodiments of the invention make it possible not only to measure the energy distribution and angular distribution, but also to measure the spectral or specular reflectivity [4], in other words the reflectivity in mirror-like reflections, of the surface by way of induced Balmer lines (reaction A) of the hydrogen atoms.

Figure 4:
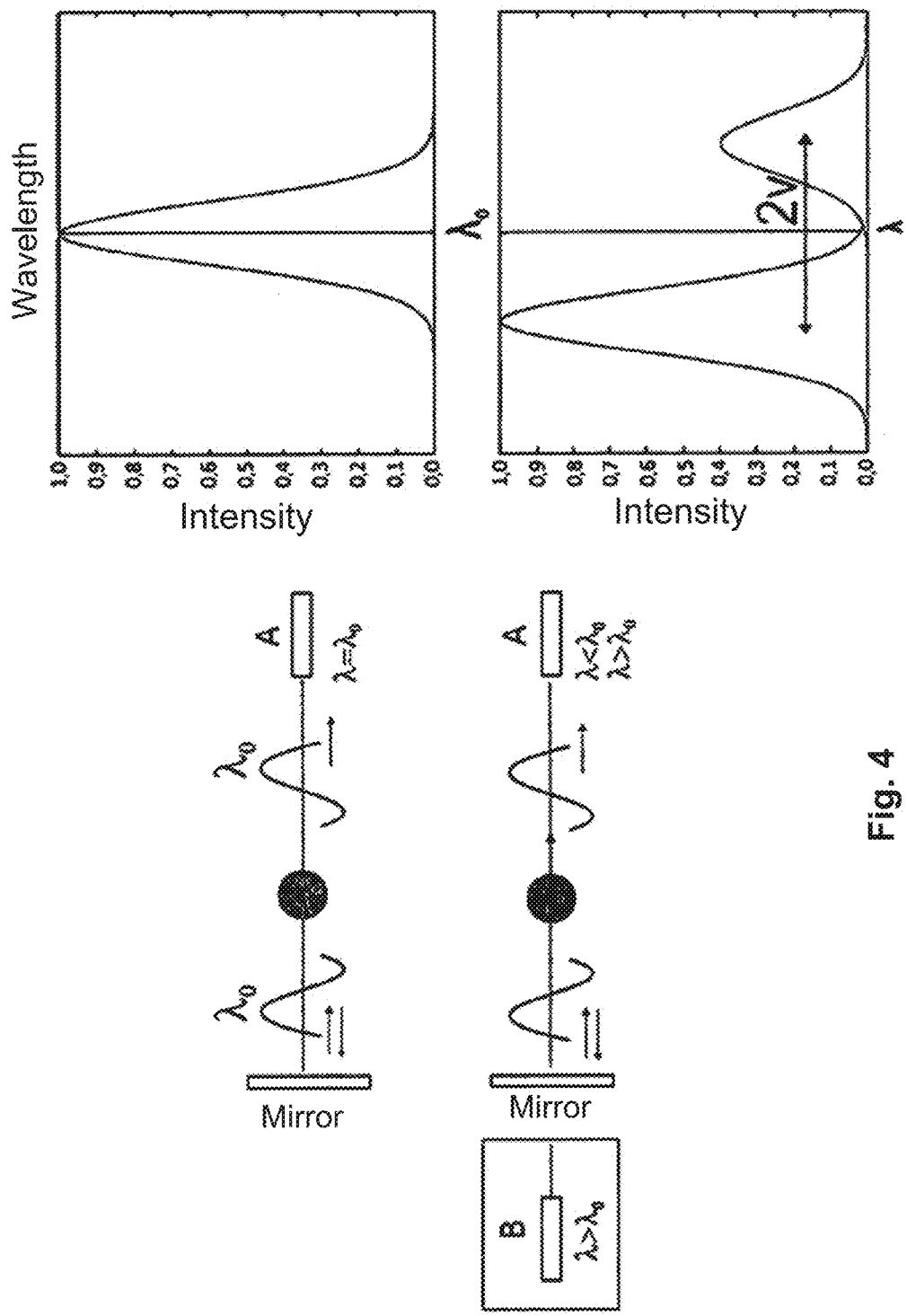
FIG. 4 is a schematic drawing of the effect of the Doppler shift in front of reflecting surfaces.

Each excited atom emits a particular number of photons, the energy of which corresponds to the energy difference between the quantum states of the atom, such as Balmer lines of the hydrogen atom (from main quantum numbers n>2 to n=2). The measured energy and the wavelength of the photons are each measured in the detector A in the standard manner (FIG. 4). If there is no relative movement between the atom and the observer (detector), this is referred to as an unshifted spectral position or wavelength. If the atom moves relative to the observer, the position of the wavelength shifts in the direction of the movement of the atom relative to the observer (detector) as a result of the Doppler Effect. FIG. 4 shows the Doppler Effect which takes place in front of a mirror of which the reflectivity is to be determined. For the stationary atom (velocity v=0), the detector A measures the photons which are moving directly from the atom toward the detector A (to the right), but also the photons which are being reflected on the reflecting surface (to the left) and then moving toward the detector. The two photon flows appear at the same position of the detector. This position corresponds to the unshifted wavelength $\lambda_0$. The reflected and unreflected photons cannot be spectrally distinguished. A measurement of the reflectivity is thus not possible for stationary atoms.

For the rapidly moving atom (v>0), the situation is different. For example, the photons which are propagating toward the detector A are detected at a blue-shifted, i.e. smaller, wavelength. By contrast, the photons which are initially propagating toward the mirror are captured with a red shift. (This situation could also be portrayed as if instead of the mirror a detector B were recording the photons moving to the left). The reflectivity of the mirror can be derived directly from the intensity ratio of the red-shifted and blue-shifted lines. The shifted lines have to be sufficiently separated from one another that they can both be measured simultaneously.

This simple solution raises two questions:
i. How can the atoms in the plasma be accelerated in front of the mirror in such a way that the two lines can be separated and clearly resolved?
ii. How is a sufficiently high line intensity achieved in low-pressure plasmas?

Questions (iii) and (iv) are substantially identical to questions or conditions (i) and (ii). The acceleration of the atoms (iii) is achieved by applying a negative potential to the surface. The high intensity of the hydrogen lines is guaranteed by process (A). As a result of the Doppler Effect, the reflection measurements of the spectral lines are clear. Since hydrogen and deuterium are the lightest atoms, the most precise measurements of the reflection are achieved when they are used. By contrast with heavier atoms, they reach the greatest velocity at the same kinetic energy, $v^2=2E/m$.

All in all, this results in a simultaneous method for measuring the reflection characteristics of hydrogen particles at the surface, in other words the energy distribution and angular distribution thereof, and for measuring the spectral reflectivity of hydrogen lines in laboratory plasmas without removing the substrate from the plasma and interrupting the plasma operation.

An in situ method according to an embodiment of the invention for determining the energy reflection and particle reflection of hydrogen or deuterium atoms was tested in a plasma having the following parameters on the linear PSI-2 system [11]: the plasma pressure was $10^{-3}$ Pa to $10^{-1}$ Pa, the plasma density was $10^{17}$ m$^{-3}$ to $10^{19}$ m$^{-3}$, the gas flows (Ar/D or Ar/H) were 10 sccm to 100 sccm, the mixing ratio of Ar/D or Ar/H was 1:1, the plasma temperature was 3 eV to 10 eV, and the applied voltage at the surface was −50 V to −200 V.

First (FIG. 5), it is shown that the signal of the reflected atoms is greatly amplified by resonance process (A). It can be seen in FIG. 5 that the emission intensity of the reflected atoms is strongly influenced by the Ar—H ratio, and basically disappears for pure D or pure Ar plasma.

The ratio of 1:1 for Ar:H or Ar:D offers the best conditions for carrying out the reflection measurements of the particles and the light.

It can be shown that it is possible to measure the energy distribution and angle distribution of the atoms when different potentials are applied to the surface of the target. FIG. 6 shows the emission of the deuterium atoms as the potential is varied at the tungsten substrate.

Figure 7:
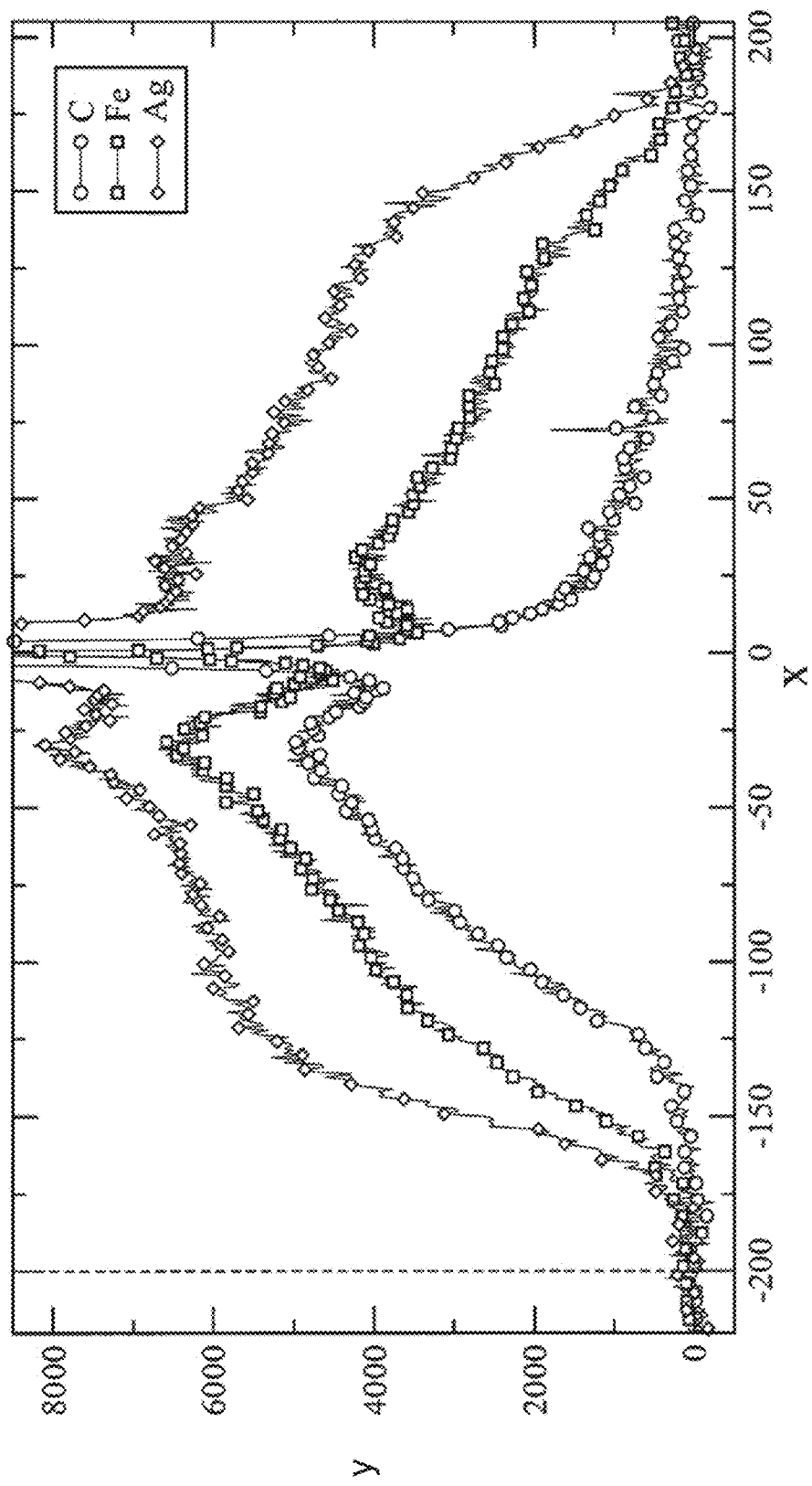
FIG. 7 shows a comparison of the energy distribution of hydrogen atoms reflected on a carbon (C), a silver (Ag) and an iron (Fe) substrate.

The average energies of the reflected atoms can even be established without detailed analysis of the data. The different symbols of the measurement curves of the drawing represent different kinetic energies of the atoms, which correspond to the applied potential of the surface. The width of the Doppler-shifted wing is proportional to the velocity of the atoms, and thus corresponds to the direct measurement variable of energy distribution. The atoms having a kinetic energy of 280 eV thus have the strongest propagation by comparison with all other atoms and the kinetic energies thereof. The measurement curve corresponding to the atoms having a kinetic energy of 100 eV has a much smaller area of the signal. The progression of the energy distribution, as described above, can thus be made use of so as to determine the material of the surface, as is frequently necessary for example in the process of surface-coating. FIG. 7 compares the energy distributions of the atoms reflected on a silver (Ag), an iron (Fe) and a carbon substrate (C) at the same applied potential (−200 V). In the case of the carbon substrate, it is possible to see the much narrower Doppler widening of the wings and thus the lower energy of the reflected H atoms (at the same applied potential) by comparison with the silver or iron substrate. As a result of the lower mass of the carbon atoms (m=12.011 $u_0$) by comparison with the iron atoms (m=55.845 $u_0$) or the silver atoms (m=107.8682 $u_0$), the hydrogen ions lose more of the incidence energy thereof upon impact with the carbon surface. This results in the reflected, neutral hydrogen atoms having a lower energy than when they strike the silver or iron substrate. Corresponding results also occur for example for the comparison between tungsten (W) substrates and aluminum (Al) substrates.

The above measurements show that the energy of the hydrogen atoms reflected on the carbon substrate is approximately 50 eV lower than the energy of the atoms reflected on the silver substrate. The simple formula [6] confirms the measured result. Accordingly, the measurement method can provide information as to the nature of the material of the surface. The measurement precision is only limited by the statistics and resolution of the detector (spectrometer) used. At a resolution $$\frac{\lambda}{\Delta\lambda}$$

of approximately $10^5$ in the visible range of the electromagnetic spectrum, it is possible to differentiate between the different metals. The ratio of the energy $E_{max}$ of a substrate comprising atoms of a higher mass to the energy $E_{max}$ of a substrate comprising atoms of a lower mass is at least 5% for the iron, silver and carbon targets mentioned herein. The different materials of the target can thus differ from one another in terms of the energy $E_{max}$. The ratio of the different energies $E_{max}$ required to distinguish the materials of targets is generally based, among other things, on the precision requirements and the available measurement times or integration times.

Figure 8:
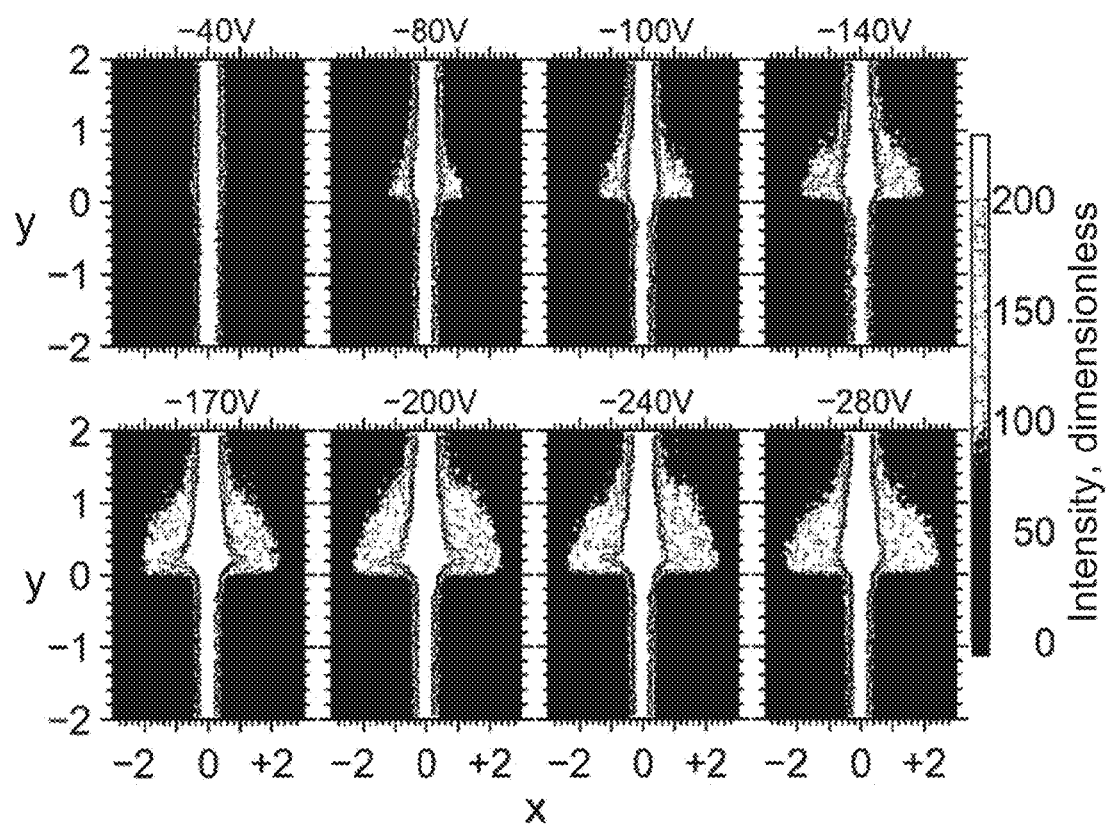
FIG. 8 shows raw data on the intensity of the emission of reflected D atoms on a W substrate for Ar-D plasmas at an angle θ=90°.

The relative progression of the emission profiles is similar for different materials. The general profile shape merely depends on the observation direction of the detector (spectrometer). The observations at different angles can be used to determine the angular distribution of the reflected atoms. FIG. 8 shows measurements for an observation at an angle of 90° to the normal, in other words with the line of sight extending parallel over the surface. The plasma conditions are identical to the conditions from FIG. 6. This observation direction is free of spectral reflection measurement; in other words in this special case the red-shifted component comes not from the reflection but directly from the particles which are moving away from the detector. Just as was shown in FIG. 6, in this case too it can be seen that the energy of the atoms varies proportionally to the applied potential. FIG. 9(a) shows the same scan again in a graph, integration having been carried out over the first 5 mm along the z-axis in front of the surface, in other words in the direction perpendicular to the surface. Below this, FIG. 9(b) shows the energy of the particles.

From FIG. 9(b), the angular distribution of the hydrogen particles can be determined. The measured data can and should be compared with theoretical models (4). FIG. 10 shows the possible angular distribution of the atoms. Thus, the measured data from FIG. 9(b) can be effectively reproduced using the angular distribution of $\cos^b(\theta)$, where b=1.0–2.0.

In a method according to an embodiment of the invention for determining the spectral reflectivity, integration may be carried out over the blue-shifted and red-shifted ranges and comprise the following steps:
 a) integrating over the blue-shifted range of the value curve from wavelength $\lambda_0-\Delta\lambda_{max}$ to wavelength $\lambda_0-\Delta\lambda_{max} \sin(\theta)$, where $\lambda_0$ corresponds to the unshifted Balmer lines. The variable $\Delta\lambda_{max}$ is the difference between the Balmer line $\lambda_0$ and the wavelength $\lambda_{max}$, which in accordance with step g) in claim 1 is associated with the energy $E_{max}$
 b) integrating over the red-shifted range of the value curve from wavelength $\lambda_0+\Delta\lambda_{max} \sin(\theta)$ to wavelength $\lambda_0+\Delta\lambda_{max}$
 c) determining the spectral reflectivity as the ratio of the smaller integral to the larger integral.

An alternative method for determining the spectral reflectivity by integrating over the blue-shifted and red-shifted ranges may comprise the following steps:
 a) integrating over the blue-shifted range of the value curve from wavelength $\lambda_0-\Delta\lambda_{max}$, which according to the method in the main claim results in the energy $E_{max}$, to wavelength $\lambda_i$, where the value $\lambda_i$ is less than $\lambda_0-\Delta\lambda_{max}\cdot\sin\theta$ with the difference $\Delta\lambda_{max}$ between wavelength $\lambda_0$, namely the wavelength of the light emitted by an atom stationary relative to the detector, and wavelength $\lambda_{max}$
 b) integrating over the red-shifted range of the value curve from a wavelength $\lambda_i'$ to the end-point $\lambda_0+\Delta\lambda_{max}$ of this range, wavelengths $\lambda_i$ and $\lambda_i'$ being selected in such a way that the two integration intervals are of the same length and $\lambda_i'$ is greater than $\lambda_0+\Delta\lambda_{max}\cdot\sin\theta$ and less than $\lambda_0+\Delta\lambda_{max}$
 c) determining the spectral reflectivity as the ratio of the smaller integral to the larger integral.

Figure 11:
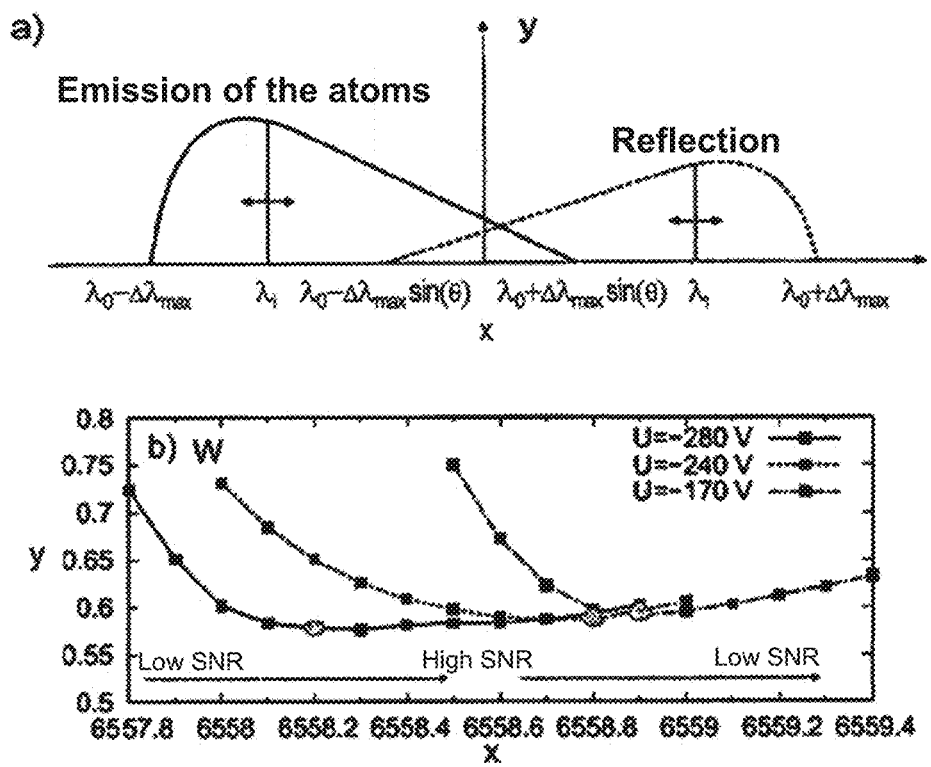
FIG. 11 shows measurements of the spectral reflection of a tungsten (W) surface using an argon-deuterium (Ar-D) plasma in which the spectral reflectivity is in the range of 0.55 to 0.6 and in which the theoretical value is 0.504 [12]

The method depicted in FIG. 4 for measuring the spectral reflectivity becomes clear in FIGS. 5 to 7. The red-shifted component is a result of the spectral reflection on the surfaces. This can be seen clearly from the example of FIG. 7. The reflection from silver is much greater than the reflection from iron and carbon. FIG. 11 shows measurements of the spectral reflection.

The measurement of the reflection or determination of the spectral reflectivity is based on the ratio of the integral between the red-shifted and the blue-shifted component as a function of the wavelength λi or λi' or the energy values Ei and Ei' associated with these wavelengths. If the relative precision of this measurement of the reflection or of the spectral reflectivity is considered, in other words the difference between the values determined according to embodiments of the invention for the spectral reflectivity and values known from the prior art from theoretical calculations or laboratory measurements for the spectral reflectivity, divided by these values known from the prior art, this precision is within 20% for all energy ranges. Thus, the measurement method offers a relatively robust alternative method for determining the reflectivity of the surface (or mirror) in situ in the plasma.

Methods according to embodiments of the invention are advantageously characterized in that the intensity values of the value curve determined at an applied voltage of zero volts are subtracted from the intensity values of a value curve determined at a voltage other than zero volts.

Advantageously, this difference has no undesirable spectral lines or artefacts in the spectrum. These artefacts may for example result from impact processes which lead to the formation of molecules, or else from other molecular processes in the plasma.

Methods according to embodiments of the invention are further advantageously characterized in that the maximum intensity value $\tilde{I}$ is determined from the blue-shifted and red-shifted wavelength ranges of the value curve determined in step e) in claim 1, the wavelength $\tilde{\lambda}$ associated with this intensity value according to the value curve, and subsequently the difference $\Delta\lambda = \lambda 0 - \tilde{\lambda}$ between the wavelength $\lambda 0$ and the wavelength $\tilde{\lambda}$, are calculated, subsequently the intensity l1 at $\lambda 0 + \Delta\lambda$ is determined, and subsequently the value of the spectral reflectivity in relation to the specular reflection or mirror reflection rs is calculated using $$r_s = \frac{l_1}{\tilde{I}}.$$

Advantageously, as a result, the value of the spectral reflectivity in relation to the specular reflection or mirror reflection can be determined. This reflection relates to the proportion of the radiation which is reflected without diffusion. If the surface is in particular completely smooth, in other words for example has no central roughness, the radiation is reflected completely without diffusion.

In an advantageous embodiment, a method is characterized by the following steps:
 a) determining the value of the maximum intensity in the wavelength range between the wavelength $\lambda_0 - \Delta\lambda_{max}$ and the wavelength $\lambda_0 - \Delta\lambda_{max} \sin(\theta)$
 b) determining the value of the maximum intensity in the wavelength range between the wavelength $\lambda_0 + \Delta\lambda_{max} \sin(\theta)$ and the wavelength $\lambda_0 + \Delta\lambda_{max}$
 c) determining the spectral reflectivity by dividing the smaller intensity value by the larger intensity value, said values having been determined in steps a) and b).

Advantageously, in this way, the value of the spectral reflectivity of the overall reflection can be determined in a simple and rapid manner. Moreover, in this case there is a better signal-to-noise ratio (SNR) (Poisson process) than if the spectral reflectivity were determined by integration over the red-shifted and blue-shifted ranges. The spectral reflectivity is thus determined to the precision of the SNR at the highest intensity. For silver as the target material, a spectral reflectivity of 0.94 in Ar:H plasma was found at −100 eV and a plasma pressure of 0.024 Pa. The theoretical value is 0.96 [12].

A method according to an embodiment of the invention is advantageously characterized in that, from a set of value curves, in which each value curve was measured at a different angle $\theta$ in a range of 0° to 90°, the value curve having the highest intensity is selected.

Advantageously, at high maximum intensity, the relevant signal values can be effectively distinguished from the intensity values of the background noise. It is therefore advantageous initially to determine the angle $\theta$ at which the maximum intensity of the value curve is highest. A method according to an embodiment of the invention is advantageously characterized in that, to determine the angle $\theta$ having the highest maximum intensity of the light, the value curve at an angle of $\theta = 90°$ between the detector and the normal vector perpendicular to the surface of the target is determined.

Advantageously, at an angle of $\theta = 90°$ only photons emitted directly by the atoms reflected from the surface are taken into account. As a result, further predictions may advantageously also be obtained, for example as to the reflection behavior of the atoms at the surface of the target.

A method according to an embodiment of the invention is advantageously characterized in that the angular distribution of the atoms after the reflection on the surface is determined by adaptation of value curves determined using a TRIM or SRIM code [5] to the value curve measured at an angle $\theta$, in particular at an angle $\theta = 90°$, the adaptation being implemented in particular by the least-squares method.

Advantageously, the angular distribution of the atoms reflected on the surface, in other words the number of atoms each reflected in the direction of an angle relative to the perpendicular to the surface or the surface normal of the target, can be determined with the detector oriented at only one angle. For this purpose, the value curve measured at this angle can be compared with value curves from theoretical models. For this purpose, for example methods based on the Monte Carlo method are suitable, such as the SRIM or TRIM codes [5] known from the prior art. For the adaptation of the values obtained from the theoretical model to the measured value curve or the fit method for determining the parameters used in programs of this type, known methods, such as the least-square fit based on the least-squares method, may be used. Thus, for example, the parameters may be selected for which the calculated model values in accordance with the least-squares method best match the measured value curve.

A method according to an embodiment of the invention is advantageously characterized in that the angular distribution of the atoms after the reflection on a planar surface of a target is determined in that, from a set of value curves which have a profile in accordance with the formula cos b($\theta$), for an angle $\theta$ relative to the perpendicular to the surface of the target or to the vertical on the surface of the target and a shaping parameter b, the value curve is determined which in accordance with the least-squares method best matches the value curve measured at an angle $\theta$, in particular an angle $\theta = 90°$.

Advantageously, the intensity I($\theta$) of the light emitted from the atoms after the reflection, as a function of an angle $\theta$ relative to the normal vector of the surface of the target at which a detector may be orientated, can be approximated by calculated value curves having a profile in accordance with cos b($\theta$). To select the suitable shaping parameter b, from the set of value curves thus calculated, in particular at values b=1 to b=2 of the shaping parameter, by the least-squares method the value curve can be selected which best matches the measured value curve. In this context, the measured value curve can be normalized in such a way that the maximum value of the intensity thereof is equal to one.

For large angles $\theta$, in particular at angles $\theta$ of more than 85° and most particularly at an angle $\theta = 90°$, the detector measures only the photons which are emitted by the reflected atoms and arrive directly at the detector, and not also the photons which are initially reflected on the surface. The dependency of the intensity of the light on the energy measured in each case of the light or of the photons, which is influenced by the Doppler shift and thus by the angle $\theta$, then also reproduces the angular distribution of the reflected atoms. The profiles of this distribution match if a suitable scaling factor is selected.

A method according to an embodiment of the invention is advantageously characterized in that a voltage of −500 V to 0 V is applied to the surface of the target.

Advantageously, by applying a voltage in this range, a kinetic energy of the ions in the plasma upon striking the target surface, the widths of the ranges of the red-shifted and blue-shifted wavelengths, and the value of the energy value $E_{max}$ can be varied. As a result, among other things, the values of the spectral reflectivity and the mass $m_2$ of the atoms of the surface can be compared for different voltages, for example so as to assess measurement errors.

A method according to an embodiment of the invention is advantageously characterized in that the pressure in the low-pressure plasma is 0.01 Pa to 0.1 Pa.

Advantageously, by using pressures of the low-pressure plasma in the range of 0.01 Pa to 0.1 Pa, for example the formation of molecules caused by impact processes can be reduced.

A method according to an embodiment of the invention is advantageously characterized in that the plasma comprises argon or hydrogen or deuterium or mixtures of these elements.

Advantageously, the energy interval of the energy value $E_{max}$ between every two adjacent elements in the periodic table, using elements having small atomic numbers Z<20 in the plasma, in particular for hydrogen or deuterium, in other words for a small, fixed value of $m_1$ for different (possible) values of the mass $m_2$ of the atoms comprised by the surface of the target, is greater than for heavier elements. Therefore, assigning the energy value $E_{max}$ to the mass of the atoms of the element comprised by the surface of the target is simpler in lighter elements having atomic numbers Z<20, in particular in hydrogen or deuterium. This is the case in particular if the surface of the target likewise comprises atoms of a light element, in particular having atomic numbers Z<20.

A method according to an embodiment of the invention is advantageously characterized in that the applied voltage is negative.

In a plasma, positively charged ions are generally present, and so the voltage for accelerating the ions toward the target surface needs to be negative.

A method according to an embodiment of the invention is advantageously characterized in that, to determine the value curve, spectral lines from the Balmer series of the atoms reflected from the surface of the target and Doppler shifts of these spectral lines are measured.

Advantageously, according to embodiments of the invention, the intensity of the spectral lines of the Balmer series or of the Balmer lines can be greatly increased, and thus the intensity distribution, angular distribution and energy distribution of the reflected light or of the reflected atoms can still be measured in the low-pressure plasma. This applies in particular to the Balmer series of hydrogen or deuterium, in particular the $H_\alpha$-, $H_\beta$- and $H_\gamma$-lines for hydrogen and the corresponding Balmer lines for deuterium.

A method according to an embodiment of the invention is advantageously characterized in that the plasma comprises mixtures of argon or krypton or hydrogen or deuterium, in particular in a mixing ratio of Ar:H=1:1 or Ar:D=1:1.

Advantageously, at this mixing ratio the emission of the Balmer lines of the reflected atoms can be particularly greatly increased.

A method according to an embodiment of the invention is advantageously characterized in that the target comprises atoms of the elements carbon or aluminum or tungsten or iron or silver.

Advantageously, the elements carbon or aluminum have atomic numbers Z<20.

A method according to an embodiment of the invention is advantageously characterized in that the target has a purity level of 95% to 100%, in particular of 99.94% to 99.999%.

Advantageously, at a high purity level of the target, the values of the energy $E_{max}$ are not distorted.

In an advantageous embodiment, a method according to an embodiment of the invention comprises the following steps:

The prerequisite for successful measurements is the application of a spectrometer having a resolution better than 10 pm to the plasma to be analyzed. The étendue of the spectrometer defines the integration time of the measurements. Care should therefore be taken that no interference occurs during the measurements.

The plasma conditions are advantageously set as follows.

The potential at the reflecting surface U is −500 V to −100 V.

The plasma pressure is 0.01 Pa to 0.10 Pa.

The gas flow for Ar/H (argon/hydrogen) or Ar/D (argon deuterium) has a ratio of approximately 1:1, or in the case of Kr/H (krypton/hydrogen) or Kr/D (krypton/deuterium) a ratio of approximately 3:7.

The measurements are taken at a particular observation angle with respect to the surface. For the measurements of the reflectivity, the angle of 0° to the surface normal is optimal. For the measurements of the angular distribution of the reflected atoms on the surface, one or more observation angles are possible.

a) Initially, a spectrum (i) without applied negative potential is measured.
b) Subsequently, a potential between −200 V and −100 V is applied to the reflecting surface and a spectrum (ii) is obtained, which already contains the information as to the spectral reflectivity of the surface.
c) Spectrum (i) is subtracted from spectrum (ii), or the intensity values of these spectra are subtracted. This difference is denoted herein as image (III), and is shown schematically in FIG. 7 and in FIG. 10.
d) The spectral reflectivity of the reflecting surface can now be calculated without any additional information by dividing the integral of the red-shifted component of the Balmer line by the integral of the blue-shifted component of the Balmer line from image (III). The measurements may be taken for Balmer lines of the hydrogen atoms. Deviations in the shape of the red-shifted and blue-shifted components indicate a diffuse surface.
e) For determining the angular distribution and energy distribution of the H or D atoms, the following procedure is required. Initially, a Monte Carlo code is used, which can predict the energy distribution and angular distribution to a first approximation. For example, the TRIM or SRIM code (www.srim.org) is very frequently used. The theoretical values of the expected spectra are obtained. The profiles are parameterized using mathematical functions. For example, the $\cos^b(\theta)$ function has become established for the angular distribution, the parameter b being an unknown variable to be determined.
f) Taking into account the set angle of the detector with respect to the surface (see FIG. 1) and the energy distribution and angular distribution in accordance with the profile $\cos^b(\theta)$, the free parameters of the distribution are adapted (for example parameter b). The adaptation takes place using a non-linear fit of the measurement in FIG. 7 and of the profile $\cos^b(\theta)$. The variables of the angular and (or) energy distribution are thus definitively determined.

A device for carrying out the method according to any of the preceding claims may for example comprise a source of low-pressure plasmas, a voltage source, a target and a photon detector [10, 11].

FIG. 1 shows the measurement setup for determining the energy distribution and angular distribution of scattered particles on a substrate surface. The setup comprises a source of ion beams, a detector and a substrate. The angle α at which the source of ion beams is orientated and the angle θ at which the detector is orientated are measured and varied relative to the normal vector to the surface or relative to the normal to the surface. The detector measures the energy and the mass of the reflected particles.

Figure 2A:
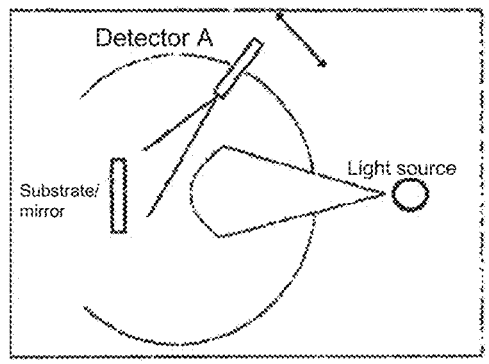
FIG. 2a) is a diagram of the laboratory measurements of reflectivities of the mirror.
Figure 2B:
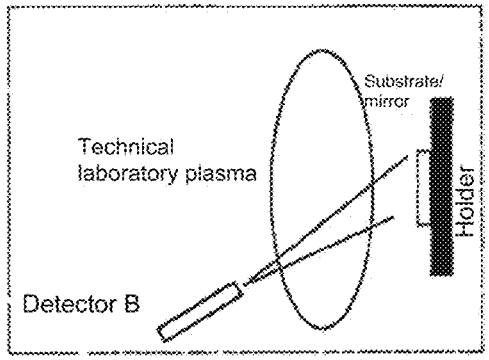
FIG. 2b) shows the application of the mirror surface in monitoring the technical process during the plasma operation.

FIG. 2a) is a diagram of the laboratory measurements of reflectivities of the mirror. The device for the measurement comprises a detector A, a light source and a mirror. FIG. 2b) shows the application of the mirror surface in monitoring the technical process during the plasma operation. The device comprises a detector, a plasma, a substrate or target, and a holder for the substrate or target.

Figure 3:
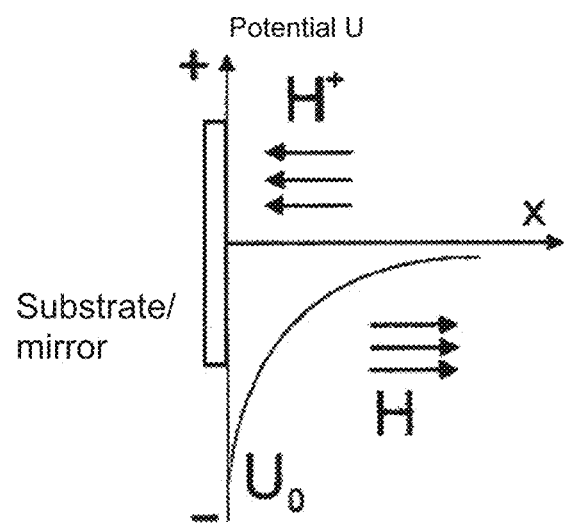
FIG. 3 is a schematic sketch for the reflection of fast plasma ions (H+) on the substrate surface and for the generation of fast neutral atoms (H) in the plasma.

FIG. 3 schematically shows how the reflection of fast plasma ions (H+) on the substrate surface leads to the production of fast neutral atoms (H) in the plasma. The ions are accelerated by a voltage −U0 onto a surface, and the neutral atoms are backscattered. The highest energy of the atoms is achieved for H or D ions, in other words for hydrogen or deuterium ions.

FIG. 4 schematically shows the effect of the Doppler shift in front of reflecting surfaces, v being the velocity of the atom. The device for determining the result of the Doppler Effect comprises a detector A and a mirror, which is arranged opposite the detector. In the upper half of the drawing, the case of the stationary atom v=0 is considered. The wavelength at the maximum intensity of the electromagnetic radiation emitted by the atom in this case or of the light is denoted $\lambda 0$. The lower part of the drawing shows the splitting of the spectrum due to the Doppler shift when the atom is moving at a final velocity v. Two intensity maxima are distinguishable at wavelengths $\lambda$ other than $\lambda 0$. The part of the spectrum or the intensity distribution which originates from the radiation reflected on the mirror is shown hatched. This radiation may also be measured by a second detector B, which is used instead of the mirror at the same location and in the same manner. The separation of the two lines depends on the velocity or kinetic energy of the atoms.

FIG. 5 shows the observation of the reflected deuterium atoms at an angle of 35° to the surface normal of the tungsten (W) substrate. The different value curves correspond to the different mixing ratios between argon (Ar) and deuterium (D) in the low-pressure plasma. The applied potential is −140 V. The blue-shifted component is used to measure the energy distribution and angular distribution. The red-shifted component is a result of the spectral reflection (see FIG. 6).

Figure 5B:
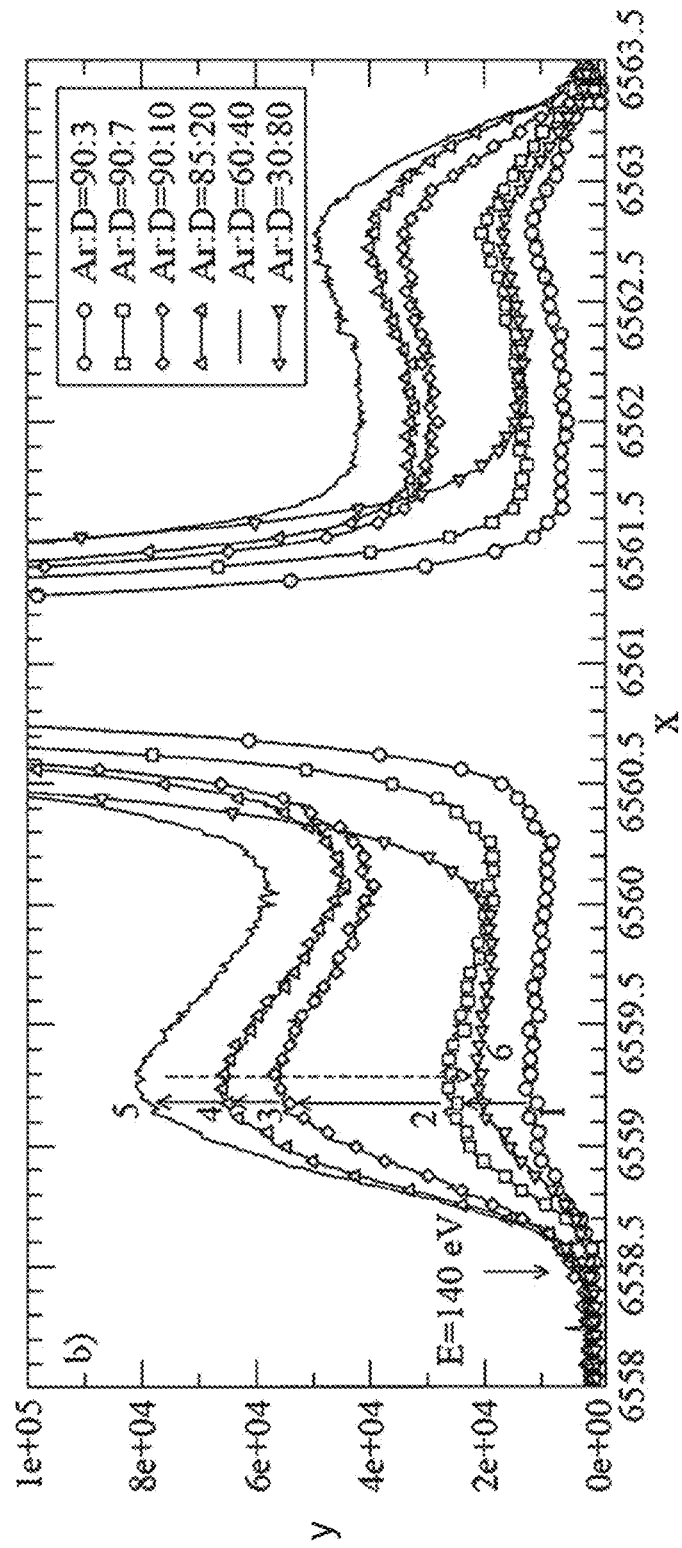
FIG. 5b) is a drawing of a bounded intensity range for this measurement in which the maxima can be detected using the Doppler shift.

FIG. 5a) shows value curves over the entire measured intensity range. FIG. 5b) shows a bounded intensity range in which the maxima can be detected using the Doppler shift. In FIG. 5a) and FIG. 5b), the wavelength in Å is plotted on the x-axis. The dimensionless intensity is plotted on the y-axis. The intensity is plotted for different mixing ratios of argon and deuterium. The mixing ratios are 90:3, 90:7, 90:10, 85:20, 60:40 and 30:80. The assignment of the intensity distributions to the respective mixing ratios can be derived from the legends in FIGS. 5a) and 5b).

In FIG. 5c), the gas flows corresponding to these mixing ratios are plotted on the y-axis in units of standard cubic centimeters sccm. The numbering is plotted on the x-axis in a manner corresponding to the numbering of the data curves in FIGS. 5a) and 5b).

Figure 6A:
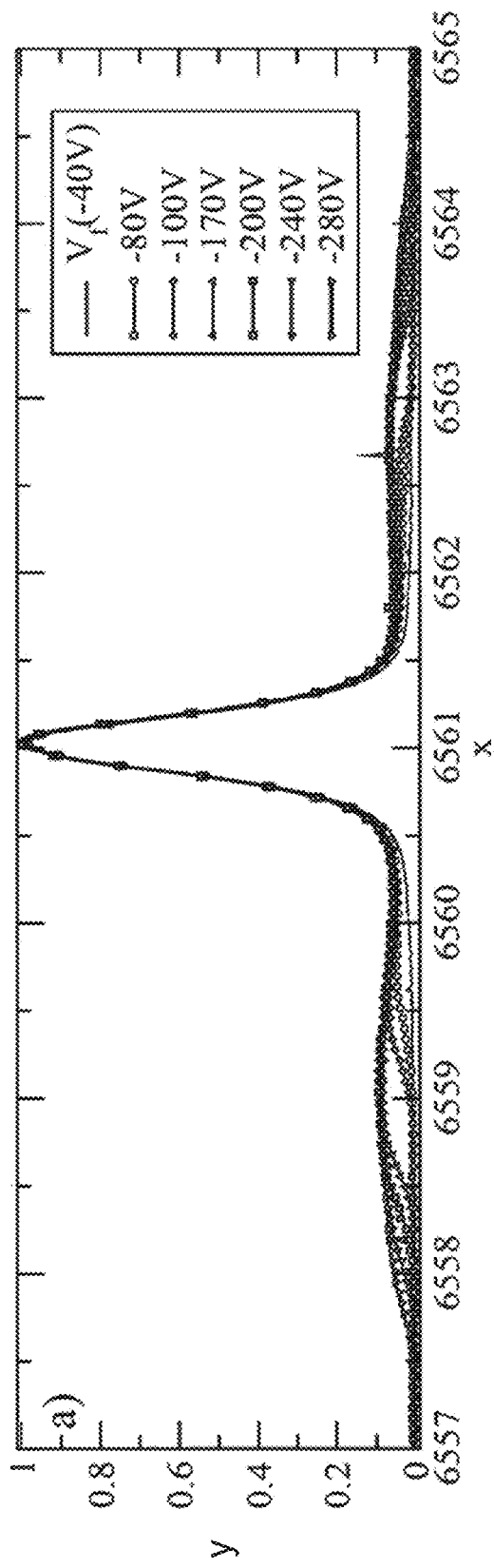
FIG. 6a) shows raw data on the emission of reflected D atoms on a tungsten substrate for Ar-D plasmas for different voltages applied to the surface of the target.
Figure 6B:
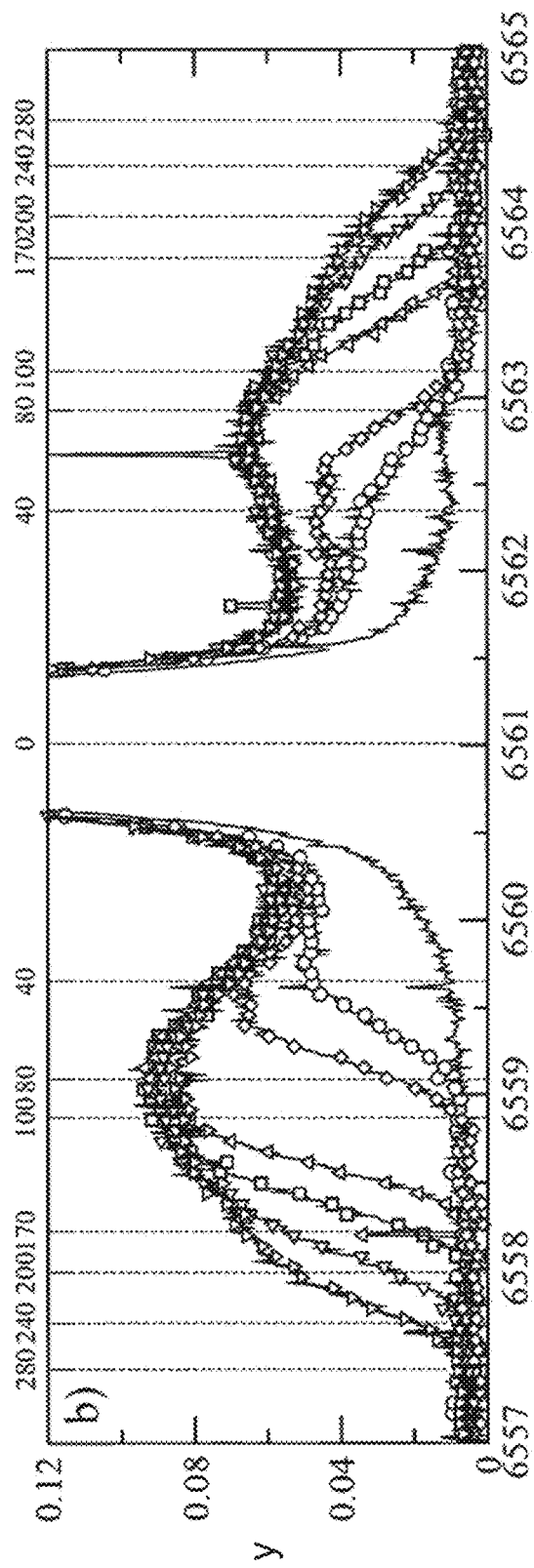
FIG. 6b) shows raw data on this measurement in an intensity range in which the maxima can be detected using the Doppler shift.

FIG. 6a) shows the raw data on the intensity of the emission of reflected D atoms on a tungsten substrate for Ar-D plasmas in a mixing ratio of 1:1. FIG. 6b) shows that the blue-shifted component (6557 Å to 6561 Å) provides the energy distribution and angular distribution of the atoms. The red-shifted component (6561 Å to 6565 Å) provides the spectral reflectivity of the W surface. The observation angle is 35° relative to the surface normal.

In FIGS. 6a) and 6b), the wavelength in A is plotted on the lower x-axis. The dimensionless intensity is plotted on the y-axis. In FIG. 6b) of the drawing, the energy of the Doppler shift in eV is plotted on the upper x-axis. The intensities are shown for different voltages applied to the surface of the target: −40 V, −80 V, −100 V, −170 V, −200 V, −240 V, −280 V. The assignment of the intensity distributions for FIGS. 6a) and 6b) to these respective voltage values can be derived from the legend in FIG. 6a).

FIG. 7 shows the comparison of the energy distribution of hydrogen atoms reflected on a carbon (C), an iron (Fe) and a silver (Ag) substrate. The applied potential is −200 V. The reflected hydrogen atoms have an increasing energy in the sequence of the carbon, iron and silver substrate, since the atomic masses of the atoms become greater in each substrate. The observation angle or detector angle is 35° relative to the surface normal.

The wavelength in Å is plotted on the x-axis. The dimensionless intensity is plotted on the y-axis. For a carbon (C), a silver (Ag) and an iron (Fe) substrate, the difference in intensity between the case where a voltage of −200 V is applied to the surface of the target and the case where no voltage is applied is shown. The purity levels of the targets are more than 99.9% in all cases. The assignment of the intensity distributions to these respective substrates can be derived from the legend in the drawing.

FIG. 8 shows raw data on the emission of reflected D atoms on a W substrate for D plasmas. The detector angle, in other words the angle θ, is 90° relative to the surface normal. The measurement provides the angular distribution of the reflected atoms in situ.

For each drawing of the intensity distribution for an individual voltage value, the distance from the surface of the target in cm is plotted on the y-axis. For each such drawing, the wavelength minus the wavelength of the α-line of the Balmer series of deuterium of 6561.01 Å, in Å, is plotted on the x-axis. The shades of grey replicate the dimensionless intensity, white representing the highest intensity and black representing the lowest intensity. The values of the voltages are −40 V, −80 V, −100 V, −140 V, −170 V, −200 V, −240 V, −280 V. The width of the Doppler-shifted ranges increases with increasing voltage.

Figure 9:
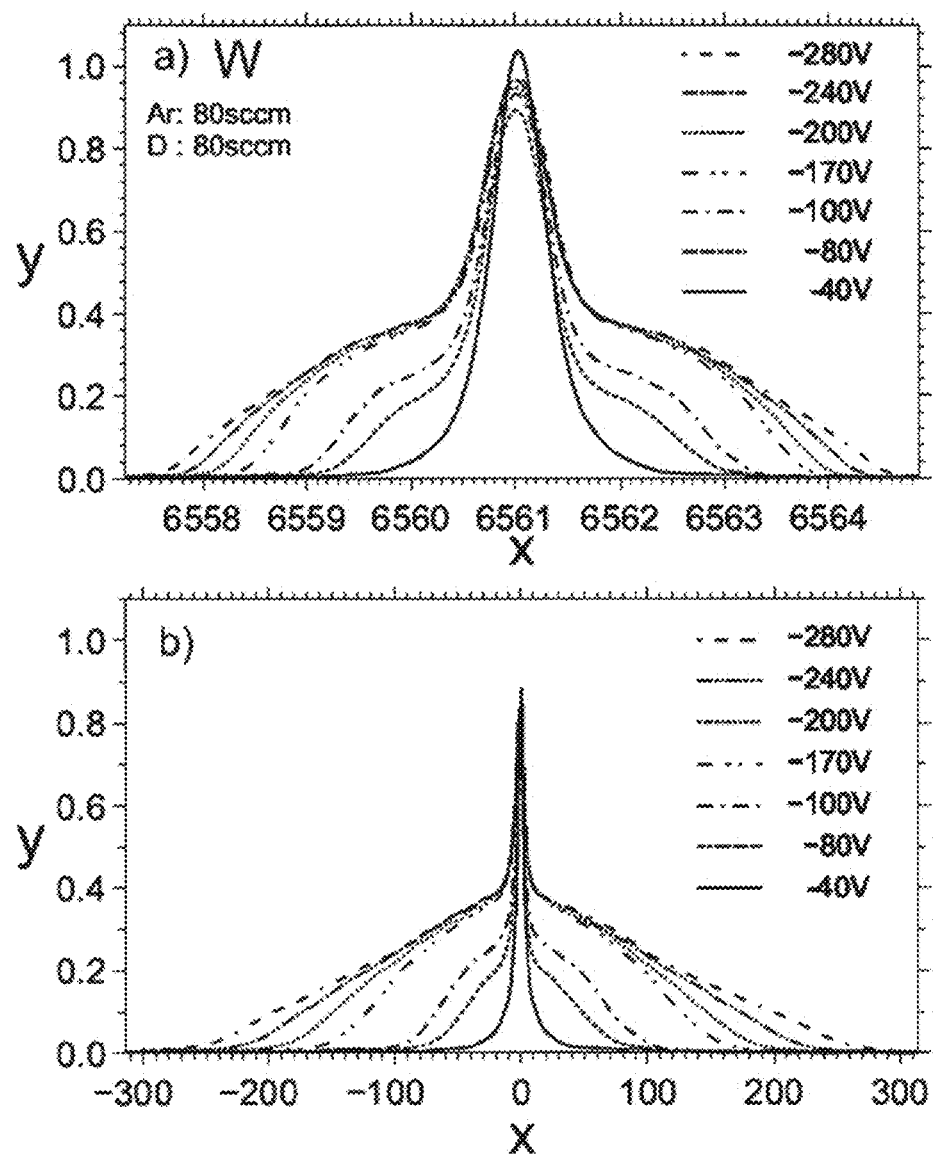
FIG. 9 shows raw data on the intensity of the emission of reflected D atoms on a W substrate for Ar-D plasmas after integration over the spatial range between the surface and an area proceeding from the shift of the surface to a distance of 5 mm in a direction perpendicular to the surface.
Figure 10:
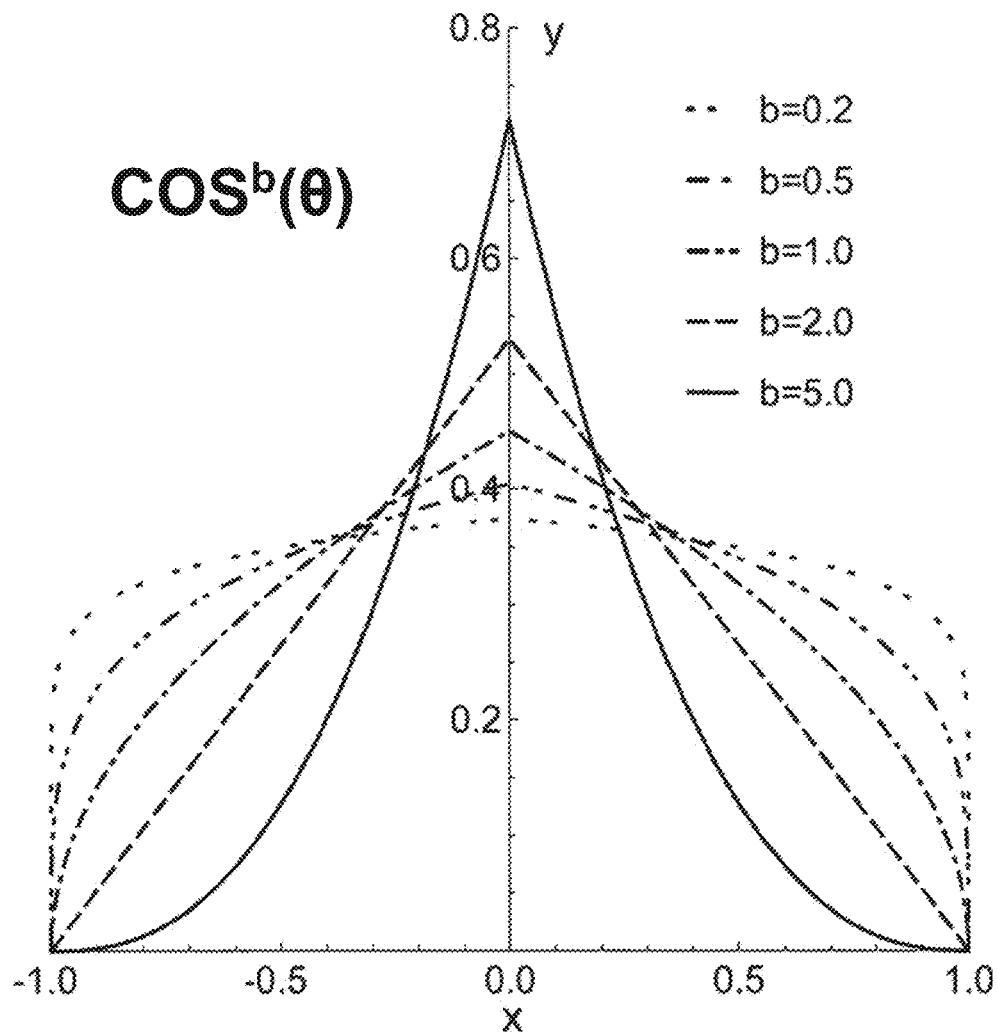
FIG. 10 shows the angular distribution of the reflected atoms, calculated for different shaping parameters b at an angle θ=90°.

FIG. 9 shows raw data on the intensity of the emission of reflected D atoms on a W substrate for Ar-D plasmas after integration over the spatial range between the surface and an area proceeding from the shift of the surface to a distance of 5 mm in a direction perpendicular to the surface. The detector angle is θ=90° relative to the surface normal.

In FIG. 9a), the wavelength in Å is plotted on the x-axis. The dimensionless intensity is plotted on the y-axis. From FIG. 9b), the angular distribution of the hydrogen particles can be determined. The measured data can be compared with theoretical models [5]. In FIG. 9b), the energy of the Doppler shift in eV is plotted on the x-axis. The dimensionless intensity is plotted on the y-axis.

The intensities in FIGS. 9a) and 9b) are shown for different voltages applied to the surface of the target: −40 V, −80 V, −100 V, −170 V, −200 V, −240 V, −280 V. The assignment of the intensity distributions to these respective voltage values can be derived from the legend on the right of FIGS. 9a) and 9b). The gas flow of the argon and deuterium of 80 sccm in each case is specified in the legend on the left of FIG. 9a).

FIG. 10 shows the angular distribution of the reflected atoms, calculated for different shaping parameters b. The observation angle or detector angle is θ=90°, as in FIG. 9.

The difference between the energy of the Doppler shift and the energy of the wavelength of the light emitted by an atom stationary relative to the detector, divided by said energy of the light of the stationary atom, is plotted on the x-axis. The dimensionless intensity is plotted on the y-axis.

The intensities are shown for different shaping factors: b=0.2, b=0.5, b=1.0, b=2.0 and b=5.0. The assignment of the intensity distributions to the shaping factors can be derived from the legend in the drawing.

FIG. 11 shows measurements of the spectral reflectivity of a tungsten (W) surface using an argon-deuterium (Ar-D) plasma having the parameters stated in the description.

In FIG. 11a), the wavelength in Å is plotted on the x-axis. The dimensionless intensity is plotted on the y-axis. The profile of the red-shifted and blue-shifted ranges of the spectrum is schematically shown when the difference in intensity between the case where a finite negative voltage is applied to the surface of the target and the case where no voltage is applied is considered.

In FIG. 11b), the wavelength in Å is plotted on the x-axis. The spectral reflectivity r is plotted on the y-axis. The values of the spectral reflectivity are calculated as follows:

integrating over the blue-shifted range of the value curve from wavelength $\lambda 0-\Delta\lambda max$, which according to the method in the main claim results in the energy Emax, to wavelength $\lambda i$, where the value $\lambda i$ is less than $\lambda 0-\Delta\lambda max \cdot \sin \theta$ with the difference $\Delta\lambda max$ between wavelength $\lambda 0$, namely the wavelength of the light emitted by an atom stationary relative to the detector, and wavelength $\lambda max$ integrating over the red-shifted range of the value curve from a wavelength $\lambda i'$ to the end-point $\lambda 0+\Delta\lambda max$ of this range, wavelengths $\lambda i$ and $\lambda i'$ being selected in such a way that the two integration intervals are of the same length and $\lambda i'$ is greater than $\lambda 0+\Delta\lambda max \cdot \sin \theta$ and less than $\lambda 0+\Delta\lambda max$ determining the spectral reflectivity as the ratio of the smaller integral to the larger integral.

FIG. 11b) shows the values of the spectral reflectivity for different wavelengths $\lambda i$ and the $\lambda i'$ which is established by the width of the integration interval by $\lambda I$ in accordance with the above method. SRN denotes the signal-to-noise ratio.

The values of the spectral reflectivity are shown for different voltages applied to the surface of the target: −280 V, −240 V, −170 V. The assignment of the values of the spectral reflectivity to the voltages can be derived from the legend in FIG. 11b).

The minima, marked in gray, of the values of the spectral reflectivities exhibit a good match for all applied voltages.

Figure 12:
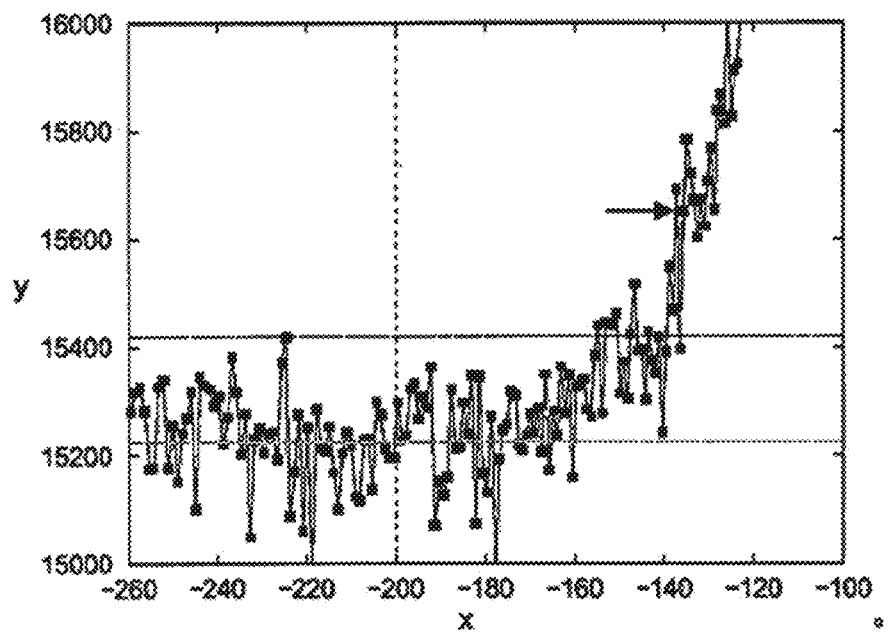
FIG. 12 shows the difference in intensities between the two cases where −200 V voltage and no voltage are applied to the surface of the target and also shows the energy value Emax where the target comprises carbon as the material and the plasma comprises a mixture of hydrogen and argon.

FIG. 12 shows the difference in intensities between the two cases where −200 V voltage and no voltage are applied to the surface of the target. In FIG. 12, the intensity is measured as the number of photoelectrons counted in or by the detector. As is known, the number of these photoelectrons is proportional to the photons striking the detector. The target comprises carbon C12 of a purity level of 99.99% as the material. To determine the surface material, hydrogen ions are accelerated toward the surface. The roughness is at the arithmetic mean roughness value Ra=0.4 µm, and the surface temperature of the target is 150° C. The detector comprises a camera of the Andor DV 8201_BV type. The detector is positioned at a distance of one meter from the surface of the target, at an angle of 35° relative to the normal vector to this surface. The spectral resolution of the detector is 5 pm and the resolution for dispersion is 1 pm. The gas flow of the argon supplied to the plasma is 40 sccm. The gas flow of the hydrogen supplied to the plasma is likewise 40 sccm. The plasma pressure is 2.5·10-4 mbar. The integration time or measurement time is 300 seconds. The size of the target is 13 mm×13 mm. The temperature of the ions is 1 eV to 3 eV, and the temperature of the electrons is 5 eV to 10 eV. The position of the energy Emax on the value curve is marked with a black arrow.

Table 1 shows the intensity differences which are obtained from raw data of this measurement, the energy being given in electron volts and the intensity being dimensionless. The value of Emax comes to Emax=−137.96 eV for an intensity difference of I=15548. The formula stated in step h) in claim 1, together with the mass of carbon for m2, results in the value of Emax being Emax=145.55 eV. This corresponds to a relative deviation of 5% if the absolute values of the energy values are considered. The value of Emax can thus be assigned to the element carbon.

TABLE 1

Difference in intensity when −200 V voltage and no voltage are applied to the surface of a target comprising carbon and the plasma comprises a mixture of hydrogen and argon in a mixing ratio of 1:1.

| Energy | Intensity |
|---|---|
| −240.8182822 | 15324 |
| −239.7922202 | 15292 |
| −238.7683488 | 15309 |
| −237.7466679 | 15221 |
| −236.7271776 | 15271 |
| −235.7098778 | 15381 |
| −234.6947686 | 15318 |
| −233.6818499 | 15201 |
| −232.6711218 | 15277 |
| −231.6625843 | 15048 |
| −230.6562373 | 15229 |
| −229.6520809 | 15249 |
| −228.650115 | 15204 |
| −227.6503397 | 15241 |
| −226.6527549 | 15244 |
| −225.6573607 | 15192 |
| −224.664157 | 15372 |
| −223.673144 | 15419 |
| −222.6843214 | 15086 |
| −221.6976894 | 15169 |
| −220.713248 | 15276 |
| −219.7309972 | 15060 |
| −218.7509368 | 15253 |
| −217.7730671 | 14997 |
| −216.7973879 | 15285 |
| −215.8238992 | 15215 |
| −214.8526012 | 15210 |
| −213.8834936 | 15254 |
| −212.9165767 | 15168 |
| −211.9518502 | 15099 |
| −210.9893144 | 15205 |
| −210.0289691 | 15242 |
| −209.0708143 | 15219 |
| −208.1148501 | 15124 |
| −207.1610765 | 15117 |
| −206.2094934 | 15227 |
| −205.2601009 | 15230 |
| −204.312899 | 15137 |
| −203.3678875 | 15299 |
| −202.4250667 | 15276 |

TABLE 1-continued

Difference in intensity when −200 V voltage and no voltage are applied to the surface of a target comprising carbon and the plasma comprises a mixture of hydrogen and argon in a mixing ratio of 1:1.

| Energy | Intensity |
|---|---|
| −201.4844364 | 15212 |
| −200.5459967 | 15195 |
| −199.6097475 | 15196 |
| −198.6756889 | 15297 |
| −197.7438208 | 15227 |
| −196.8141433 | 15237 |
| −195.8866563 | 15324 |
| −194.9613599 | 15333 |
| −194.0382541 | 15267 |
| −193.1173388 | 15309 |
| −192.1986141 | 15288 |
| −191.2820799 | 15363 |
| −190.3677363 | 15070 |
| −189.4555832 | 15154 |
| −188.5456207 | 15127 |
| −187.6378487 | 15159 |
| −186.7322673 | 15323 |
| −185.8288765 | 15213 |
| −184.9276762 | 15216 |
| −184.0286665 | 15298 |
| −183.1318473 | 15239 |
| −182.2372187 | 15349 |
| −181.3447807 | 15073 |
| −180.4545332 | 15346 |
| −179.5664762 | 15166 |
| −178.6806099 | 15131 |
| −177.796934 | 15272 |
| −176.9154488 | 14987 |
| −176.036154 | 15192 |
| −175.1590499 | 15246 |
| −174.2841363 | 15257 |
| −173.4114132 | 15319 |
| −172.5408807 | 15313 |
| −171.6725388 | 15220 |
| −170.8063874 | 15208 |
| −169.9424266 | 15238 |
| −169.0806563 | 15278 |
| −168.2210766 | 15241 |
| −167.3636875 | 15287 |
| −166.5084889 | 15207 |
| −165.6554809 | 15351 |
| −164.8046634 | 15171 |
| −163.9560364 | 15280 |
| −163.1096001 | 15236 |
| −162.2653543 | 15364 |
| −161.423299 | 15277 |
| −160.5834343 | 15349 |
| −159.7457602 | 15158 |
| −158.9102766 | 15327 |
| −158.0769835 | 15331 |
| −157.2458811 | 15340 |
| −156.4169692 | 15284 |
| −155.5902478 | 15271 |
| −154.765717 | 15386 |
| −153.9433767 | 15440 |
| −153.123227 | 15278 |
| −152.3052679 | 15446 |
| −151.4894993 | 15443 |
| −150.6759213 | 15442 |
| −149.8645338 | 15461 |
| −149.0553369 | 15314 |
| −148.2483306 | 15374 |
| −147.4435148 | 15305 |
| −146.6408895 | 15424 |
| −145.8404549 | 15516 |
| −145.0422107 | 15393 |
| −144.2461572 | 15395 |
| −143.4522941 | 15302 |
| −142.6606217 | 15430 |
| −141.8711398 | 15376 |
| −141.0838484 | 15352 |
| −140.2987476 | 15418 |
| −139.5158374 | 15242 |
| −138.7351177 | 15392 |
| −137.9565886 | 15548 |
| −137.18025 | 15469 |
| −136.406102 | 15691 |
| −135.6341446 | 15397 |
| −134.8643777 | 15651 |
| −134.0968013 | 15783 |

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCES

[1] Andersen H H. et al., Nucl. Instrum. and Meth. in Phys. Res. B 6 459 (1985)
[2] Feder R. et al., Nucl. Instrum, and Meth. in Phys. Res. B 316 198 (2013)
[3] Cooksey C., Nadal M., Allen D W, Hauer K O, Höpe A, *Applied Optics* 54 4006 (2015)
[4] Howell J R, Siegel R and Mengüc M P, "Thermal Radiation Heat Transfer", CRC Press, Taylor and Francis Group LCC, p. 70 (2011)
[5] TRIM/SRIM Code: *Stopping and Range of Ions in Matter*, http://www.srim.org
[6] Alfold T L, Feldman L C, Mayer J W, *Fundamentals of Nanoscale Film Analysis*, Springer, Berlin (2007) ISBN: 978-0-387-29260-1
[7] Babkina T. et al, Europhys. Letters 72 235 (2005)
[8] Adamov M. R. G., Obradović B. M., Kuraica M. M., Konjević N., *IEEE Trans. Plasma. Sci.* 31, 444 (2003); Adamov M. G., Kuraica M. M., Konjević N., *Eur. Phys. J. D* 28, 393 (2004)
[9] Phelps A. V., Phys. Rev. E 79 066401 (2009)

[10] Brandt C. et al, O3.J107, 42nd European Physical Society Conference on Plasma Physics, Lisbon (2015).
[7] Babkina T. et al, Europhys. Letters 72 235 (2005)
[11] Kreter et al, Fusion Sci. Technol. 68 8 (2015)
[12] WEB link: www.refractiveindex.info

The invention claimed is:

1. A method for in situ determination of surface characteristics of conductive targets, the method comprising:
   a) generating a low-pressure plasma in front of a surface of a target;
   b) applying a voltage to the surface of the target;
   c) orientating at least one light-sensitive detector at an angle θ relative to a perpendicular to the surface of the target;
   d) measuring an intensity of light emitted by electrically neutral atoms generated by conversion from ions which are accelerated out of the low-pressure plasma by the applied voltage toward the surface of the target and subsequently reflected thereon, and which thus exchange suitable charges with the surface to reach electrical neutrality;
   e) determining a value curve comprising wavelengths and an intensity associated with each wavelength, of the light which, as a result of Doppler shifts, has a red-shifted wavelength range having smaller wavelengths than a wavelength $\lambda_0$ of the light emitted by atoms stationary relative to the detector and a blue-shifted range having wavelengths greater than $\lambda_0$;
   f) determining a velocity v of a atoms which emit light of a wavelength λ from the value curve using $$v = \frac{\lambda}{\lambda - \lambda_0} \cdot c,$$

where c is the speed of light, and from this determining respective kinetic energies E of the atoms using $\varepsilon = 1/2 m_1 v^2$, where $m_1$ is a mass of each of the reflected atoms;
   g) determining an energy value $E_{max}$ as a smallest of the measured wavelengths of a particular energy from which all values of the intensity of the value curve are greater than or equal to an intensity value of background noise of the detector signal; and
   h) determining a mass $m_2$ of atoms of the surface using the formula:

$$E_{max} = \left[ \frac{(m_2^2 - m_1^2 \sin^2\theta)^{1/2} - m_2 \cdot \cos\theta}{m_3 + m_2} \right]^2 \cdot E_0,$$

where $E_0$ is the kinetic energy of each of the ions upon striking the surface and is equal to the absolute value of the applied voltage.

2. The method according to claim 1, wherein intensity values of the value curve determined at an applied voltage of zero volts are subtracted from intensity values of a value curve determined at a voltage other than zero volts.

3. The method according to claim 1, wherein a maximum intensity value $\tilde{I}$ is determined from the blue-shifted and red-shifted wavelength ranges of the value curve determined in step e), the wavelength $\tilde{\lambda}$ associated with this intensity value according to the value curve, and subsequently the difference $\Delta\lambda = \lambda_0 - \tilde{\lambda}$ between the wavelength $\lambda_0$ and the wavelength $\tilde{\lambda}$, are calculated, subsequently the intensity $I_1$ at $\lambda_0 + \Delta\lambda$ is determined, and subsequently a spectral reflectivity in relation to the specular reflection $r_s$ is calculated using $$r_s = \frac{I_1}{\tilde{I}}.$$

4. The method according to claim 1, further comprising:
   determining a first value being a maximum intensity in a wavelength range between the wavelength $\lambda_0 - \Delta\lambda_{max}$ and the wavelength $\lambda_0 - \Delta\lambda_{max} \sin(\theta)$;
   determining a second value being a maximum intensity in a wavelength range between the wavelength $\lambda_0 + \Delta\lambda_{max} \sin(\theta)$ and the wavelength $\lambda_0 + \Delta\lambda_{max}$; and
   determining a spectral reflectivity by dividing the smaller of the first value and the second value by the larger of the first value and the second value.

5. The method according to claim 1, wherein from a set of value curves, in which each value curve was measured at a different angle θ in a range of 0° to 90°, a value curve having a highest intensity is selected.

6. The method according to claim 1, wherein, to determine an angle θ having a highest maximum intensity of light, a value curve at an angle of θ=90° between the detector and the normal vector perpendicular to the surface of the target is determined.

7. The method according to claim 6, wherein an angular distribution of atoms after reflection on the surface is determined by adaptation of value curves determined using a TRIM or SRIM code to the value curve measured at an angle θ, the adaptation being implemented in particular by a least-squares method.

8. The method according to claim 6, wherein an angular distribution of the atoms after reflection on a planar surface of a target is determined in that, from a set of value curves which have a profile in accordance with the formula $\cos^b(\theta)$, for an angle θ relative to the perpendicular to the surface of the target and a shaping parameter b, the value curve is determined which in accordance with the least-squares method best matches the value curve measured at an angle θ.

9. The method according to claim 1, wherein a voltage of −500 V to 0 V is applied to the surface of the target.

10. The method according to claim 1, wherein a pressure in the low-pressure plasma is 0.01 Pa to 0.1 Pa.

11. The method according to claim 1, wherein the plasma comprises argon or hydrogen or deuterium or mixtures of these elements.

12. The method according to claim 1, wherein, to determine the value curve, spectral lines from the Balmer series of atoms reflected from the surface of the target and Doppler shifts of these spectral lines are measured.

13. The method according to claim 1, wherein the plasma comprises mixtures of argon or krypton or hydrogen or deuterium.

14. The method according to claim 1, wherein the target comprises atoms of carbon or aluminum.

15. The method according to claim 1, wherein the target has a purity level of 95% to 100%.

16. A device for carrying out the method according to claim 1, comprising a source of low-pressure plasmas, a voltage source, a target, and a photon detector.

* * * * *